(12) United States Patent  
Karantonis et al.

(10) Patent No.: US 12,403,317 B2  
(45) Date of Patent: Sep. 2, 2025

(54) PROGRAMMING OF NEUROMODULATION THERAPY

(71) Applicant: Saluda Medical Pty Limited, Level 1 (AU)

(72) Inventors: Dean Michael Karantonis, Artarmon (AU); Robert Bruce Gorman, Artarmon (AU); Matthew Marlon Williams, Artarmon (AU); Samuel Nicholas Gilbert, Artarmon (AU); Milan Obradovic, Artarmon (AU)

(73) Assignee: Saluda Medical Pty Limited, Macquarie Park (AU)

( * ) Notice: Subject to any disclaimer, the term of this patent is extended or adjusted under 35 U.S.C. 154(b) by 371 days.

(21) Appl. No.: 17/936,340

(22) Filed: Sep. 28, 2022

(65) Prior Publication Data

US 2023/0096151 A1  Mar. 30, 2023

(30) Foreign Application Priority Data

Sep. 28, 2021  (AU) .................... 2021903100

(51) Int. Cl.
*A61N 1/36* (2006.01)
*A61N 1/02* (2006.01)
*A61N 1/05* (2006.01)

(52) U.S. Cl.
CPC .......... *A61N 1/3614* (2017.08); *A61N 1/025* (2013.01); *A61N 1/0551* (2013.01); *A61N 1/36139* (2013.01)

(58) Field of Classification Search
None
See application file for complete search history.

(56) References Cited

U.S. PATENT DOCUMENTS

| | | | |
|---|---|---|---|
| 7,853,330 B2 | 12/2010 | Bradley et al. | |
| 8,131,357 B2 | 3/2012 | Bradley et al. | |
| 8,463,402 B2 | 6/2013 | Zhu et al. | |
| 10,434,308 B2 | 10/2019 | Isaacson et al. | |
| 10,588,698 B2 | 3/2020 | Parker et al. | |
| 2017/0259065 A1* | 9/2017 | Baru ................ | A61N 1/36153 |

(Continued)

FOREIGN PATENT DOCUMENTS

| | | |
|---|---|---|
| WO | 2012155183 A1 | 11/2012 |
| WO | 2012155188 A1 | 11/2012 |

(Continued)

*Primary Examiner* — Ankit D Tejani  
(74) *Attorney, Agent, or Firm* — Barnes & Thornburg LLP

(57) ABSTRACT

Disclosed is an implantable device for lead offset determination, comprising first and second electrode leads. A stimulus is delivered from one lead to tissue, and a signal is sensed from the tissue by the other lead. The sensed signal is processed to produce a measure of a stimulus artefact present in the signal. The stimulus artefact measure is used to produce a measure of an offset between the first electrode lead and the second electrode lead, such as by applying a distance-squared analytical model to measures of stimulus artefact obtained from at least two sense electrodes. And/or, a compound action potential evoked by the stimulus is sensed from neural tissue, a latency of the evoked compound action potential is measured, and a measure of an offset between the first electrode lead and the second electrode lead is produced from the latency.

26 Claims, 13 Drawing Sheets

(56) References Cited

U.S. PATENT DOCUMENTS

2022/0040485 A1 2/2022 Li et al.
2022/0096841 A1 3/2022 Jackson et al.

FOREIGN PATENT DOCUMENTS

| WO | 2015074121 A1 | 5/2015 |
| WO | 2016090420 A1 | 6/2016 |
| WO | 2017219096 A1 | 12/2017 |
| WO | 2020082126 A1 | 4/2020 |
| WO | 2020124135 A1 | 6/2020 |
| WO | 2022170388 A1 | 8/2022 |

* cited by examiner

PROGRAMMING OF NEUROMODULATION THERAPY

CROSS REFERENCE TO RELATED APPLICATION

This application claims the benefit of Australian Provisional Patent Application No. 2021903100, which is incorporated herein by reference.

TECHNICAL FIELD

The present invention relates to neuromodulation, and in particular to a system and method for determining a relative positional offset between two implanted electrode leads of a neuromodulation device.

BACKGROUND OF THE INVENTION

There are a range of situations in which it is desirable to apply neural stimuli in order to alter neural function, a process known as neuromodulation. For example, neuromodulation is used to treat a variety of disorders including chronic neuropathic pain, Parkinson's disease, and migraine. A neuromodulation system applies an electrical pulse (stimulus) to neural tissue (fibres, or neurons) in order to generate a therapeutic effect. In general, the electrical stimulus generated by a neuromodulation system evokes a neural action potential in a neural fibre which then has either an inhibitory or excitatory effect. Inhibitory effects can be used to modulate an undesired process such as the transmission of pain, or excitatory effects can be used to cause a desired effect such as the contraction of a muscle.

When used to relieve neuropathic pain originating in the trunk and limbs, the electrical pulse is applied to the dorsal column (DC) of the spinal cord, a procedure referred to as spinal cord stimulation (SCS). Such a system typically comprises an implanted electrical pulse generator, and a power source such as a battery that may be transcutaneously rechargeable by wireless means, such as inductive transfer. An electrode array is connected to the pulse generator, and is positioned adjacent the target neural fibre(s) in the spinal cord, typically in the dorsal epidural space above the dorsal column. An electrical pulse of sufficient intensity applied to the target neural fibres by a stimulus electrode causes the depolarisation of neurons in the fibres, which in turn generates a response known as an action potential in the fibres. Action potentials propagate along the fibres in orthodromic (towards the head, or rostral) and antidromic (towards the cauda, or caudal) directions. The fibres being stimulated in this way inhibit the transmission of pain from a region of the body innervated by the target neural fibres (the dermatome) to the brain. To sustain the pain relief effects, stimuli are applied repeatedly, for example at a frequency in the range of 30 Hz-100 Hz.

The action potentials generated by the depolarisation of a large number of fibres by a stimulus sum to form a measurable signal known as an evoked compound action potential (ECAP). Accordingly, an ECAP is the sum of responses from a large number of single fibre action potentials. The ECAP generated from the depolarisation of a group of similar fibres may be measured at a measurement electrode as a positive peak potential, then a negative peak, followed by a second positive peak. This morphology is caused by the region of activation passing the measurement electrode as the action potentials propagate along the individual fibres.

Approaches proposed for obtaining a neural measurement are described by the present applicant in International Patent Publication No. WO2012/155183, the content of which is incorporated herein by reference.

To better understand the effects of neuromodulation and/or other neural stimuli, it is desirable to accurately detect and record a neural response such as a CAP evoked by the stimulus. However, this can be a difficult task as an observed CAP signal will typically have a maximum amplitude of a few tens of microvolts or less, whereas a stimulus applied to evoke the CAP is typically several volts. Electrode artefact usually results from the stimulus, and manifests after the stimulus has completed as a decaying output of several millivolts or hundreds of microvolts throughout the time that the CAP occurs, presenting a significant obstacle to isolating the much smaller CAP of interest. As the neural response can be contemporaneous with the stimulus and/or the stimulus artefact, CAP measurements present a difficult challenge of implant design. In practice, many non-ideal aspects of a circuit lead to artefact, and as these mostly have a decaying exponential characteristic which can be of either positive or negative polarity, identification and elimination of sources of artefact can be laborious. Evoked responses are less difficult to detect when they appear later in time than the artefact, or when the signal-to-noise ratio is sufficiently high. The artefact is often restricted to a time of 1-2 ms after the stimulus and so, provided the neural response is detected after this time window, a response measurement can be more easily obtained. This is the case in surgical monitoring where there are large distances (e.g. more than 12 cm for nerves conducting at 60 ms-1) between the stimulating and measurement electrodes so that the propagation time from the stimulus site to the measurement electrodes exceeds 2 ms.

However, to characterize the responses from the dorsal column, high stimulation currents and close proximity between electrodes are required. Similarly, any implanted neuromodulation device will necessarily be of compact size, so that for such devices to monitor the effect of applied stimuli, the stimulus electrode(s) and measurement electrode (s) will necessarily be in close proximity. In such situations the measurement process must overcome artefact directly.

For effective and comfortable operation, it is necessary to maintain stimulus intensity above a recruitment threshold. Stimuli below the recruitment threshold will fail to recruit sufficient neurons to generate action potentials with a therapeutic effect. In almost all neuromodulation applications, response from a single class of fibre is desired, but the stimulus waveforms employed can evoke action potentials in other classes of fibres which cause unwanted side effects. In pain relief, is therefore necessary to apply stimuli which are below a comfort threshold, above which uncomfortable or painful percepts arise due to over-recruitment of $A\beta$ fibres. When recruitment is too large, $A\beta$ fibres produce uncomfortable sensations. Stimulation at high intensity may even recruit $A\delta$ fibres, which are sensory nerve fibres associated with acute pain, cold and pressure sensation. It is therefore desirable to maintain stimulus intensity within a therapeutic range between the recruitment threshold and the comfort threshold.

The task of maintaining appropriate neural recruitment is made more difficult by electrode migration (change in position over time) and/or postural changes of the implant recipient (patient), either of which can significantly alter the neural recruitment arising from a given stimulus, and therefore the therapeutic range. There is room in the epidural space for the electrode array to move, and such array movement from migration or posture change alters the electrode-to-fibre distance and thus the recruitment efficacy of a given stimulus. Moreover, the spinal cord itself can move within the cerebrospinal fluid (CSF) with respect to the dura. During postural changes, the amount of CSF and/or the distance between the spinal cord and the electrode can change significantly. This effect is so large that postural changes alone can cause a previously comfortable and effective stimulus regime to become either ineffectual or painful.

Another control problem facing neuromodulation systems of all types is achieving neural recruitment at a sufficient level for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Attempts have been made to address such problems by way of feedback or closed-loop control, such as using the methods set forth in International Patent Publication No. WO2012/155188 by the present applicant. Feedback control seeks to compensate for relative nerve/electrode movement by controlling the intensity of the delivered stimuli so as to maintain a substantially constant neural recruitment. The intensity of a neural response to stimulus, such as an amplitude of an ECAP, may be used as a feedback variable representative of the amount of neural recruitment. A signal representative of the ECAP may be generated by a measurement electrode in electrical communication with the recruited neural fibres, and processed to obtain the feedback variable. Based on the response intensity, the intensity of the applied stimulus may be adjusted to maintain the response within a therapeutic range.

A functional feedback loop can also produce useful data for live operation and/or post-analysis, such as observed neural response amplitude and applied stimulus intensity. However, device operation at tens of Hz over the course of hours or days quickly produces large volumes of such data which far exceed an implanted device's data storage capacities.

Neuromodulation implants are sometimes configured to have more than one electrode lead, for a range of reasons. For example, the use of two leads allows surgical implantation of the leads in a manner which results in a partially overlapping positioning of the electrode array of each lead in a rostro-caudal direction, and a lateral spacing of the electrode arrays in the medio-lateral direction. Partial overlapping of the electrode arrays in the rostro-caudal direction allows the implanted device configuration to have an element of adjustability whereby a total length of nerve addressed by the two arrays can be selectively controlled, for example to meet anatomical constraints or due to therapeutic needs of the particular patient. Further, lateral spacing of the electrode arrays in the medio-lateral direction can facilitate electrical current steering whereby stimulation is preferentially directed spatially to a particular nerve site by appropriately dividing the stimulus across multiple electrodes proximal to that site. However, separately implantable leads add complexities in that the therapy delivered from two such leads depends to a significant degree on knowledge of the relative position of the leads to each other as well as to the nerve, and moreover in that each lead can migrate not only with respect to the nerve, but also can migrate independently of the other lead. The absolute position of the leads in the target tissue, and the relative position of the leads to each other, are crucial for delivering a suitable therapy such as a comfortable paraesthesia sensation in the subject covering the affected areas. The absolute and relative position of the leads, which includes medio-lateral and rostro-caudal position relative to the spinal cord, has a direct influence on the efficacy of the treatment being provided. Therefore, a change in the absolute or relative lead position may result in significant changes in the effectiveness of the therapy which affects the patient satisfaction.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood to mean that the element may be any one of the listed options, or may be any combination of two or more of the listed options.

SUMMARY OF THE INVENTION

According to a first aspect, the present invention provides an implantable device for lead offset determination, the device comprising:

a first electrode lead comprising a first plurality of electrodes;

a second electrode lead comprising a second plurality of electrodes;

a stimulus source for providing a stimulus to be delivered from one or more stimulus electrodes to tissue proximal to the one or more stimulus electrodes, the one or more stimulus electrodes being selected from the first plurality of electrodes and the second plurality of electrodes;

measurement circuitry for recording from one or more sense electrodes a signal sensed from the tissue and resulting from the stimulus, the one or more sense electrodes being selected from the first plurality of electrodes and the second plurality of electrodes;

wherein at least one electrode of the first plurality of electrodes serves as either a stimulus electrode or as a sense electrode, and wherein at least one electrode of the second plurality of electrodes serves as either a stimulus electrode or as a sense electrode; and a processor configured to process the signal from the measurement circuitry in order to produce a measure of a stimulus artefact present in the signal; and the processor further configured to process the measure of the stimulus artefact to produce a measure of an offset between the first electrode lead and the second electrode lead.

According to a second aspect, the present invention provides a method for lead offset determination, the method comprising:

delivering a stimulus from one or more stimulus electrodes to tissue proximal to the one or more stimulus electrodes, the one or more stimulus electrodes being selected from a first plurality of electrodes of a first electrode lead and a second plurality of electrodes of a second electrode lead;

recording from one or more sense electrodes a signal sensed from the tissue and resulting from the stimulus, the one or more sense electrodes being selected from the first plurality of electrodes and the second plurality of electrodes;

wherein at least one electrode of the first plurality of electrodes serves as either a stimulus electrode or as a sense electrode, and wherein at least one electrode of the second plurality of electrodes serves as either a stimulus electrode or as a sense electrode; and processing the signal in order to produce a measure of a stimulus artefact present in the signal; and processing the measure of the stimulus artefact to produce a measure of an offset between the first electrode lead and the second electrode lead.

According to a third aspect, the present invention provides a non-transitory computer readable medium for lead offset determination, comprising instructions which, when executed by one or more processors, causes performance of the following:

delivering a stimulus from one or more stimulus electrodes to tissue proximal to the one or more stimulus electrodes, the one or more stimulus electrodes being selected from a first plurality of electrodes of a first electrode lead and a second plurality of electrodes of a second electrode lead;

recording from one or more sense electrodes a signal sensed from the tissue and resulting from the stimulus, the one or more sense electrodes being selected from the first plurality of electrodes and the second plurality of electrodes;

wherein at least one electrode of the first plurality of electrodes serves as either a stimulus electrode or as a sense electrode, and wherein at least one electrode of the second plurality of electrodes serves as either a stimulus electrode or as a sense electrode; and processing the signal in order to produce a measure of a stimulus artefact present in the signal; and processing the measure of the stimulus artefact to produce a measure of an offset between the first electrode lead and the second electrode lead.

In some embodiments of the invention, producing the measure of stimulus artefact may comprise identifying a strength, such as an amplitude, power or energy, of a decaying output arising in the signal after conclusion of the stimulus. The strength of such signals may be measured as a peak stimulus artefact magnitude observed following completion of the stimulus, for example in the period of 0-1000 μs post-stimulus. The strength of the stimulus artefact may be measured as an area under a curve of the decaying output, for example in the period of 0-1000 μs post-stimulus. The strength of the stimulus artefact may be measured as a power or energy of the decaying output, for example in the period of 0-1000 μs post-stimulus.

In some embodiments of the invention, a stimulus configuration is selected to maximise a stimulus artefact resulting from application of the stimulus. Selection of the stimulus configuration may comprise selection of a stimulus phase configuration and/or a stimulus electrode configuration. Notably, such embodiments thus seek the opposite outcome to typical neurostimulation systems having measurement circuitry, which typically seek to minimise stimulus artefact which is considered to be noise, to allow measurement of physiological responses which are the signals of interest. In contrast, embodiments of the present invention may instead exploit a stimulus configuration which seeks to maximise stimulus artefact, as stimulus artefact is the signal of interest in this technique for lead offset measurement. Maximising stimulus artefact as the signal of interest, relative to other signals which in this application are considered to be noise, thus may improve measurement sensitivity of the lead offset measurements based on stimulus artefact. For example, the stimulus phase configuration may comprise a biphasic pulse, noting that biphasic stimulation typically produces greater stimulus artefact than optimised triphasic stimulation. Alternatively, the stimulus phase configuration may comprise a triphasic stimulus whereby a ratio of charge of a first phase relative to a third phase is adjusted so as to maximise or increase stimulus artefact. In another alternative, monophasic stimulation may be utilised to create large stimulus artefact, with charge recovery effected for example by passive grounding of a case electrode and/or by delivering a charge recovery pulse after completion of the lead offset measurement.

In still further embodiments the stimulus electrode configuration may be selected to maximise a stimulus artefact resulting from application of the stimulus by configuring the stimulation such that, in a relation of stimulus artefact as arising relative to distance from the stimulus electrode, a maximal region of the artefact is substantially co-located with the or a sense electrode. In embodiments where the lead offset measurement is based on stimulus artefact measurements obtained respectively from more than one sense electrode in response to more than one applied stimulus, the stimulus electrode configuration may be revised for subsequent stimuli, in order to co-locate the maximal region of the artefact with the or a sense electrode in use at the time. While noting that lead offset may not be precisely known a priori to permit absolute co-location, such embodiments may serve to refine an initial imprecise estimation of an absolute lead offset, or may be applied in a relative manner by shifting the maximal region of stimulus artefact by an amount equal to a known spacing between electrodes even if an absolute offset is not yet known. Techniques to co-locate stimulus artefact minima set forth in International Patent Publication No. WO2020/082126, the contents of which are incorporated herein by reference, may be applied mutatis mutandis to desirably locate stimulus artefact maxima in such embodiments of the present invention. For example, any suitable number of stimulus phases, any suitable number of stimulus poles, and/or any suitable balancing or unbalancing of current delivered by each phase or by each pole, may be selected for this purpose.

Additionally, or alternatively, in some embodiments of the invention a stimulus artefact resulting from application of the stimulus is maximised by connecting an impedance to at least one passive electrode proximal to the sense electrode(s), the impedance being configured to increase stimulus artefact arising at the sense electrode(s).

In embodiments where the stimulus configuration is selected to maximise a stimulus artefact resulting from application of the stimulus so as to facilitate the lead offset measurement, the implantable device may further be configured to subsequently alter the stimulus configuration after completion of measurement of the lead offset, so as to revert to a second stimulus configuration which provides for minimisation of stimulus artefact to facilitate measurement of other signals of interest such as evoked compound action potentials. In such embodiments the altering of the stimulus configuration may comprise altering a stimulus phase configuration and/or a stimulus electrode configuration.

Additionally, or alternatively, in some embodiments of the invention a stimulus electrode configuration may be selected so as to spatially constrain a maximal region of a stimulus artefact resulting from application of the stimulus. Measurements based on a spatially constrained stimulus artefact field may be advantageous in facilitating detection of stimulus artefact field strength differences at different sense electrodes, thereby improving positional sensitivity of a resultant lead offset measurement. The stimulus electrode configuration may spatially constrain a maximal region of a stimulus artefact by utilising a shielded anode tripolar stimulus electrode configuration, preferably by using consecutive electrodes along the lead, or alternatively by using a spaced tripole stimulus electrode configuration having unused electrodes between each pair of stimulus electrodes in use.

In some embodiments, the stimulus electrodes are all located on the first electrode lead, a sense electrode is located on the second lead, and a sense reference electrode is located on the first electrode lead. In such embodiments, the method may be applied repeatedly for unchanged electrodes on the first lead and with iteratively altered selection of which of the second plurality of electrodes to use as the sense electrode. For example, the method may be iteratively repeated so as to consecutively obtain a stimulus artefact measurement from every one of the second plurality of electrodes.

In some embodiments of the invention, the measure of the offset is produced by applying a distance-squared analytical model to measures of stimulus artefact obtained from at least two sense electrodes. In such embodiments the model may assume that the peak-to-peak magnitude of the artefact decreases proportionately with distance squared. For example, the model may comprise a relationship:

$$A(d) = \frac{a}{(d-b)^2 + c^2}$$

where A(d) is a function of measured stimulus artefact A relative to a distance d of the sense electrode from the stimulus electrode, and a, b and c are fitting parameters, with b constituting the lead offset measurement. In such embodiments, an iterative fitting process may be applied to seek values for a, b and c which best fit the model to the measures of stimulus artefact. Preferred embodiments further provide for automated discarding of invalid fittings. For example, a fitting may be determined as being invalid and discarded if: fitting fails to converge or is too slow to converge; and/or $a \leq 0$ (the curve has no peak or is inverted); and/or the value of b places the curve peak beyond the electrode array and/or the peak height of the fitted curve differs from observed data peak height by more than a permitted margin; and/or the fitted curve peak height fails to exceed the raw data mean by a sufficient margin. In the event of automated discarding of an invalid fitting, a fallback offset measure may be output comprising an indication that a stimulus artefact peak occurs at whichever electrode recorded maximal artefact.

In some embodiments of the invention, the measure of the offset is produced by applying a fractional pole components model of artefact, in which each edge of a voltage step in the chosen stimulation pulse(s) is treated as a singularity at which is defined an independent set of step and impulse components based on a constant phase element (CPE) characterisation of the electrode-tissue interface. Such embodiments may for example include component scalar values introduced to reflect step-specific unknown variances as for example may arise with tissue impedance. Such embodiments may further provide for staged fitting and recombination of the component scalar values so as to identify which measurement electrode on the second lead lies closest to the stimulus site of the first lead, and thus identify the lead offset.

According to a fourth aspect the present invention provides an implantable device for lead offset determination, the device comprising:
  a first electrode lead comprising a first plurality of electrodes;
  a second electrode lead comprising a second plurality of electrodes;
  a stimulus source for providing a stimulus to be delivered from one or more stimulus electrodes to neural tissue proximal to the one or more stimulus electrodes, the one or more stimulus electrodes being selected from the first plurality of electrodes and the second plurality of electrodes;
  measurement circuitry for recording from one or more sense electrodes a compound action potential sensed from the neural tissue and evoked by the stimulus, the one or more sense electrodes being selected from the first plurality of electrodes and the second plurality of electrodes;
  wherein at least one electrode of the first plurality of electrodes serves as either a stimulus electrode or as a sense electrode, and wherein at least one electrode of the second plurality of electrodes serves as either a stimulus electrode or as a sense electrode; and
  a processor configured to process the recording of the evoked compound action potential in order to produce a measure of a latency of the evoked compound action potential as observed at the one or more sense electrodes; and the processor further configured to process the measure of the latency to produce a measure of an offset between the first electrode lead and the second electrode lead.

According to a fifth aspect, the present invention provides a method for lead offset determination, the method comprising:
  delivering a stimulus from one or more stimulus electrodes to neural tissue proximal to the one or more stimulus electrodes, the one or more stimulus electrodes being selected from a first plurality of electrodes of a first electrode lead and a second plurality of electrodes of a second electrode lead;
  recording from one or more sense electrodes a compound action potential sensed from the neural tissue and evoked by the stimulus, the one or more sense electrodes being selected from the first plurality of electrodes and the second plurality of electrodes;
  wherein at least one electrode of the first plurality of electrodes serves as either a stimulus electrode or as a sense electrode, and wherein at least one electrode of the second plurality of electrodes serves as either a stimulus electrode or as a sense electrode; and
  processing the recording of the evoked compound action potential in order to produce a measure of a latency of the evoked compound action potential as observed at the one or more sense electrodes; and processing the measure of the latency to produce a measure of an offset between the first electrode lead and the second electrode lead.

According to a sixth aspect, the present invention provides a non-transitory computer readable medium for lead offset determination, comprising instructions which, when executed by one or more processors, causes performance of the following:

delivering a stimulus from one or more stimulus electrodes to neural tissue proximal to the one or more stimulus electrodes, the one or more stimulus electrodes being selected from a first plurality of electrodes of a first electrode lead and a second plurality of electrodes of a second electrode lead;

recording from one or more sense electrodes a compound action potential sensed from the neural tissue and evoked by the stimulus, the one or more sense electrodes being selected from the first plurality of electrodes and the second plurality of electrodes;

wherein at least one electrode of the first plurality of electrodes serves as either a stimulus electrode or as a sense electrode, and wherein at least one electrode of the second plurality of electrodes serves as either a stimulus electrode or as a sense electrode; and processing the recording of the evoked compound action potential in order to produce a measure of a latency of the evoked compound action potential as observed at the one or more sense electrodes; and processing the measure of the latency to produce a measure of an offset between the first electrode lead and the second electrode lead.

Some embodiments of the fourth to sixth aspects of the invention may further comprise: obtaining a second recording of the evoked compound action potential from the measurement circuitry via one or more second sense electrodes which is/are distinct from the one or more sense electrodes; processing the second recording of the evoked compound action potential in order to produce a measure of a second latency of the evoked compound action potential as observed at the one or more second sense electrodes; and processing the measure of the second latency to produce the measure of an offset between the first electrode lead and the second electrode lead. For example, the second latency may be compared with the latency in order to generate the measure of the offset.

Some embodiments of the fourth to sixth aspects of the invention may further comprise obtaining respective recordings of the evoked compound action potential from the measurement circuitry via a plurality of sense electrodes located on the first lead, and further obtaining respective recordings of the evoked compound action potential from the measurement circuitry via a plurality of sense electrodes located on the second lead. For example, respective recordings of the evoked compound action potential may in some embodiments be obtained from all available electrodes located on the second lead and/or from all available electrodes located on the first lead. By obtaining recordings of a single ECAP from a plurality of sense electrodes, a conduction velocity of the ECAP can be determined, which in turn can be used to improve lead offset determinations.

In some embodiments of the fourth to sixth aspects of the invention, the one or more stimulus electrodes all reside on the first electrode lead.

In some embodiments of the fourth to sixth aspects of the invention, a first sense electrode resides on the second electrode lead and a second sense electrode resides on the first electrode lead. Such embodiments may further comprise altering a selection of the first sense electrode from the electrodes of the second electrode lead, and repeating the delivering, recording and processing steps in respect of the altered first sense electrode.

In some embodiments of the fourth to sixth aspects of the invention the first electrode lead and second electrode lead are configured to be separately implantable.

In some embodiments of the fourth to sixth aspects of the invention the device comprises a case housing the stimulus source, the measurement circuitry and the processor. In such embodiments the case may comprise a header configured to receive a proximal end of the first electrode lead and configured to receive a proximal end of the second electrode lead.

In some embodiments of the first to sixth aspects of the invention the lead offset measurement may comprise a measure of an offset relative to an axis of propagation of a nerve addressed by the electrodes, such as a measure of a rostro-caudal offset between the first electrode lead and the second electrode lead. Additionally, or alternatively, the lead offset measurement may comprise a measure of an offset laterally relative to an axis of propagation of a nerve addressed by the electrodes, such as a measure of a medio-lateral offset between the first electrode lead and the second electrode lead.

In some embodiments of the third aspect or sixth aspect of the invention, the instructions contained upon the non-transitory computer readable medium may comprise a clinical programming application, the clinical programming application further configured to provide clinical programming functions for an implantable device comprising the first and second electrode leads, so as to program the implantable device based on the measure of the offset. Other embodiments of the third aspect or sixth aspect of the invention may comprise a firmware implementation.

References herein to estimation, determination, comparison and the like are to be understood as referring to an automated process carried out on data by a processor operating to execute a predefined procedure suitable to effect the described estimation, determination and/or comparison step(s). The technology disclosed herein may be implemented in hardware (e.g., using digital signal processors, application specific integrated circuits (ASICs) or field programmable gate arrays (FPGAs)), or in software (e.g., using instructions tangibly stored on non-transitory computer-readable media for causing a data processing system to perform the steps described herein), or in a combination of hardware and software. The disclosed technology can also be embodied as computer-readable code on a computer-readable medium. The computer-readable medium can include any data storage device that can store data which can thereafter be read by a computer system. Examples of the computer-readable medium include read-only memory ("ROM"), random-access memory ("RAM"), magnetic tape, optical data storage devices, flash storage devices, or any other suitable storage devices. The computer-readable medium can also be distributed over network-coupled computer systems so that the computer-readable code is stored and/or executed in a distributed fashion.

BRIEF DESCRIPTION OF THE DRAWINGS

One or more implementations of the invention will now be described with reference to the accompanying drawings, in which.

DETAILED DESCRIPTION OF THE PREFERRED EMBODIMENTS

Figure 1:
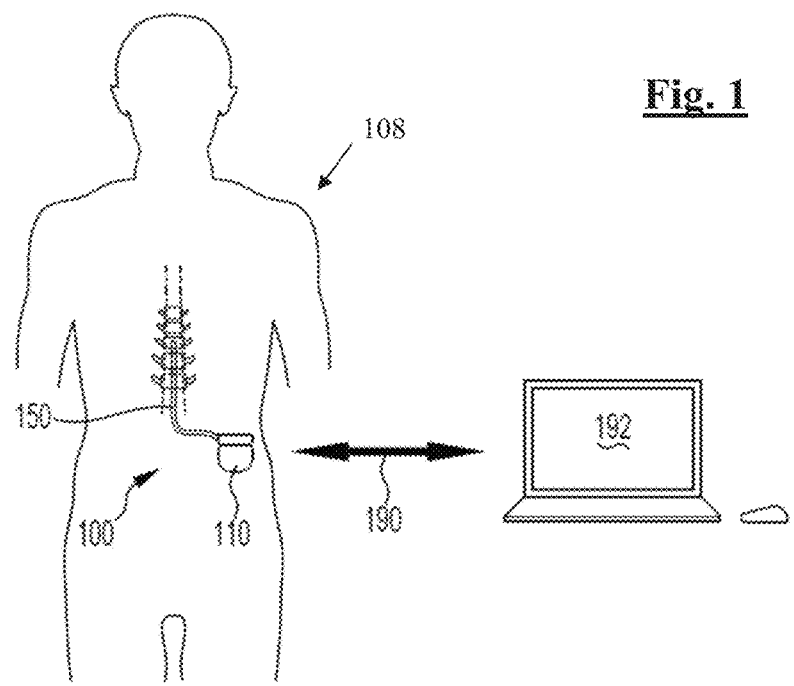
FIG. 1 schematically illustrates an implanted spinal cord stimulator, according to one implementation of the present technology.

FIG. 1 schematically illustrates an implanted spinal cord stimulator 100 in a patient 108, according to one implementation of the present technology. Stimulator 100 comprises an electronics module 110 implanted at a suitable location. In one implementation, stimulator 100 is implanted in the patient's lower abdominal area or posterior superior gluteal region. In other implementations, the electronics module 110 is implanted in other locations, such as a flank or subclavicular. Stimulator 100 further comprises an electrode array 150 implanted within the epidural space and connected to the module 110 by a suitable lead. The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for stimulation and measurement. The electrodes may pierce or affix directly to the tissue itself.

Numerous aspects of operation of implanted stimulator 100 may be programmable by an external computing device 192, which may be operable by a user such as a clinician or the patient 108. Moreover, implanted stimulator 100 serves a data gathering role, with gathered data being communicated to external device 192 via a transcutaneous communications channel 190. Communications channel 190 may be active on a substantially continuous basis, at periodic intervals, at non-periodic intervals, or upon request from the external device 192. The external device may thus provide a clinical interface configured to program the neuromodulation device and recover data stored on the neuromodulation device. This configuration is achieved by program instructions collectively referred to as the Clinical Programming Application (CPA) and stored in an instruction memory of the clinical interface.

Figure 2:
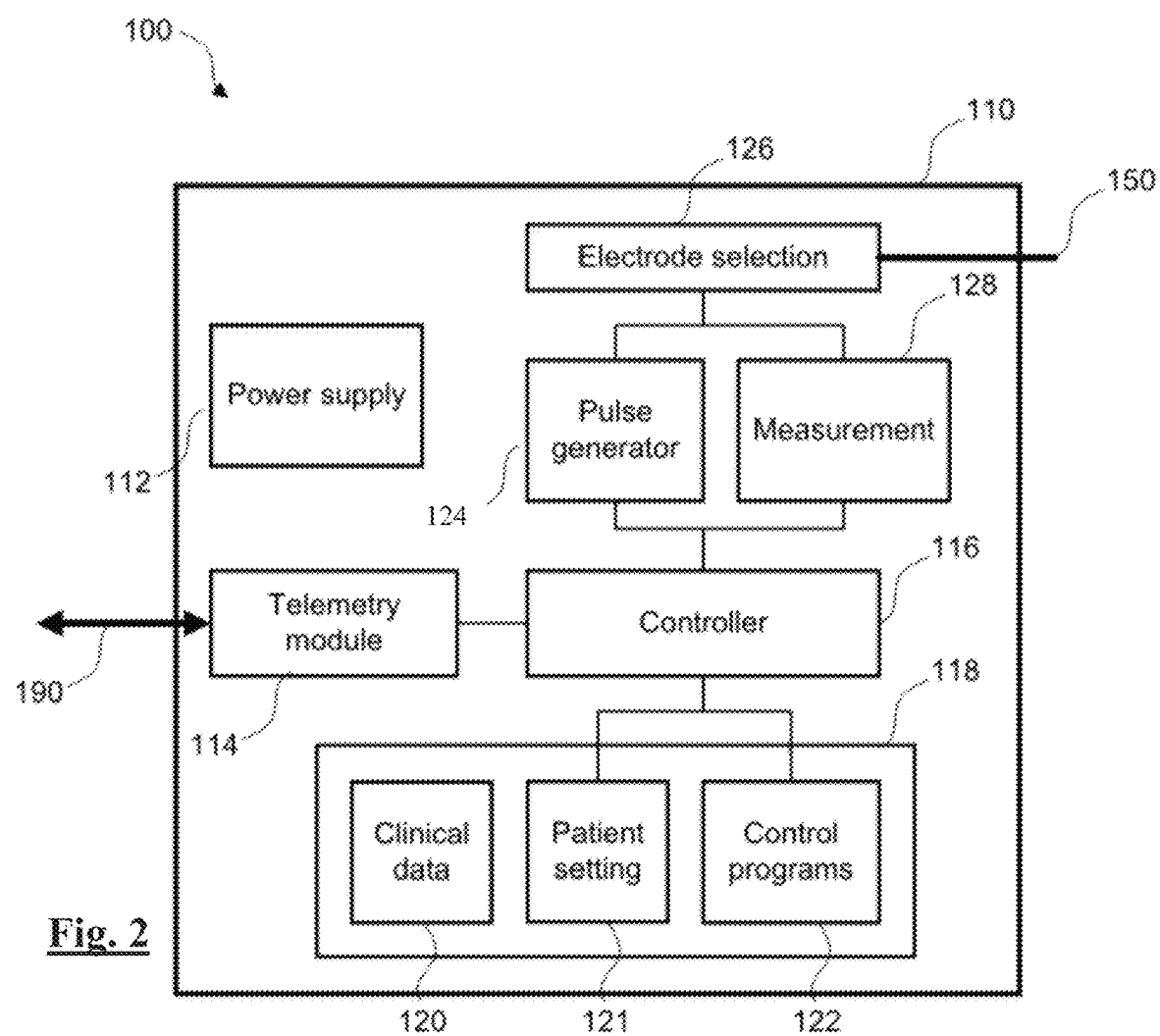
FIG. 2 is a block diagram of the stimulator of FIG. 1.

FIG. 2 is a block diagram of the stimulator 100. Electronics module 110 contains a battery 112 and a telemetry module 114. In implementations of the present technology, any suitable type of transcutaneous communication 190, such as infrared (IR), radiofrequency (RF), capacitive and inductive transfer, may be used by telemetry module 114 to transfer power and/or data to and from the electronics module 110 via communications channel 190. Module controller 116 has an associated memory 118 storing one or more of clinical data 120, patient settings 121, control programs 122, and the like. Controller 116 controls a pulse generator 124 to generate stimuli, such as in the form of pulses, in accordance with the patient settings 121 and control programs 122. Electrode selection module 126 switches the generated pulses to the selected electrode(s) of electrode array 150, for delivery of the pulses to the tissue surrounding the selected electrode(s). Measurement circuitry 128, which may comprise an amplifier and/or an analog-to-digital converter (ADC), is configured to process measurements of neural responses sensed at measurement electrode(s) of the electrode array 150 as selected by electrode selection module 126.

Figure 3:
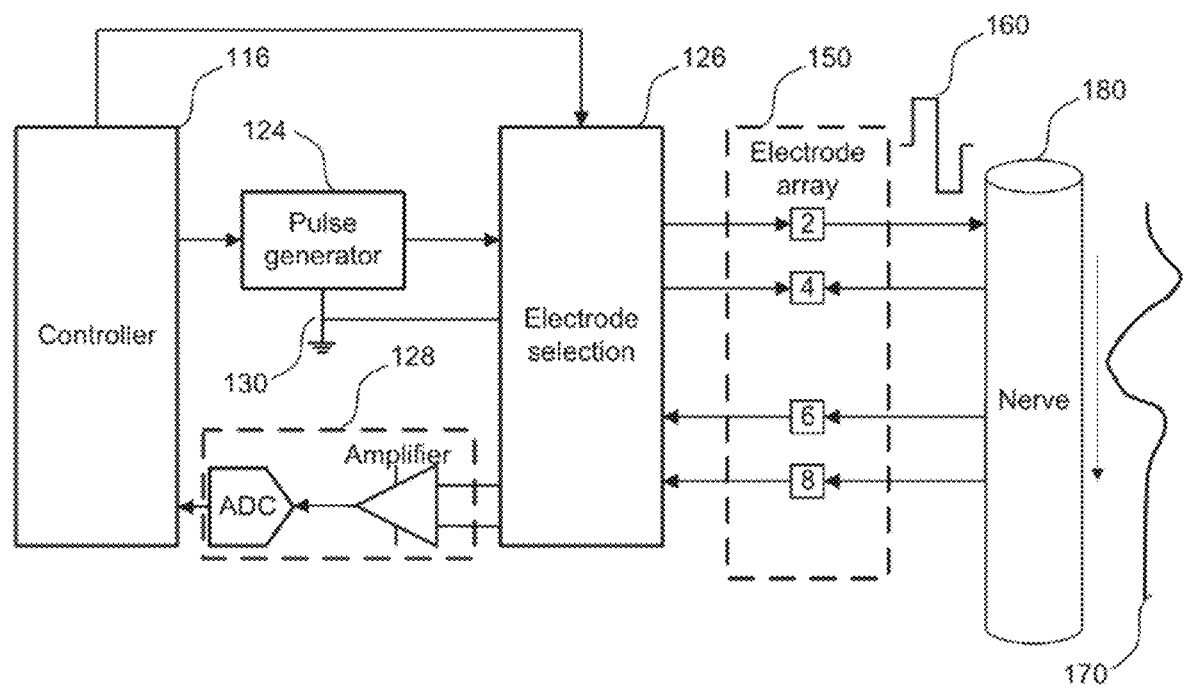
FIG. 3 is a schematic illustrating interaction of the implanted stimulator of FIG. 1 with a nerve.

FIG. 3 is a schematic illustrating interaction of the implanted stimulator 100 with a nerve 180 in the patient 108. In the implementation illustrated in FIG. 3 the nerve 180 may be located in the spinal cord, however in alternative implementations the stimulator 100 may be positioned adjacent any desired neural tissue including a peripheral nerve, visceral nerve, parasympathetic nerve or a brain structure. Electrode selection module 126 selects a stimulus electrode 2 of electrode array 150 through which to deliver a pulse from the pulse generator 124. A pulse may comprise one or more phases, e.g. a biphasic stimulus pulse 160 comprises two phases. The electrode selection module 126 selects a stimulus electrode 2 to deliver the pulse to surrounding tissue including nerve 180. Electrode selection module 126 also selects a return electrode 4 of the electrode array 150 for stimulus charge recovery in each phase, to maintain a zero net charge transfer. The use of two electrodes in this manner for delivering and recovering current in each stimulus phase is referred to as bipolar stimulation. Alternative embodiments may apply other forms of bipolar stimulation, or may use a greater number of stimulus electrodes. Electrode selection module 126 is illustrated as connecting to a ground 130 of the pulse generator 124 to enable stimulus charge recovery via the return electrode 4. However, other connections for charge recovery may be used in other implementations.

Delivery of an appropriate stimulus from stimulus electrodes 2 and 4 to the nerve 180 evokes a neural response comprising an evoked compound action potential 170

(ECAP) which will propagate along the nerve 180 as illustrated, for therapeutic purposes, which in the case of a spinal cord stimulator for chronic pain may be to create paraesthesia at a desired location. To this end, the stimulus electrodes 2 and 4 are used to deliver stimuli periodically at any therapeutically suitable frequency, for example 30 Hz, although other frequencies may be used including frequencies as high as the kHz range. In alternative implementations, stimuli may be delivered in a non-periodic manner such as in bursts, or sporadically, as appropriate for the patient 108. To "fit" the stimulator 100 to the patient 108, a clinician may cause the stimulator 100 to deliver stimuli of various configurations which seek to produce a sensation that is experienced by the user as paraesthesia. When a stimulus configuration is found which evokes paraesthesia in a location and of a size which is congruent with the area of the patient's body affected by pain, the clinician nominates that configuration for ongoing use.

Figure 5:
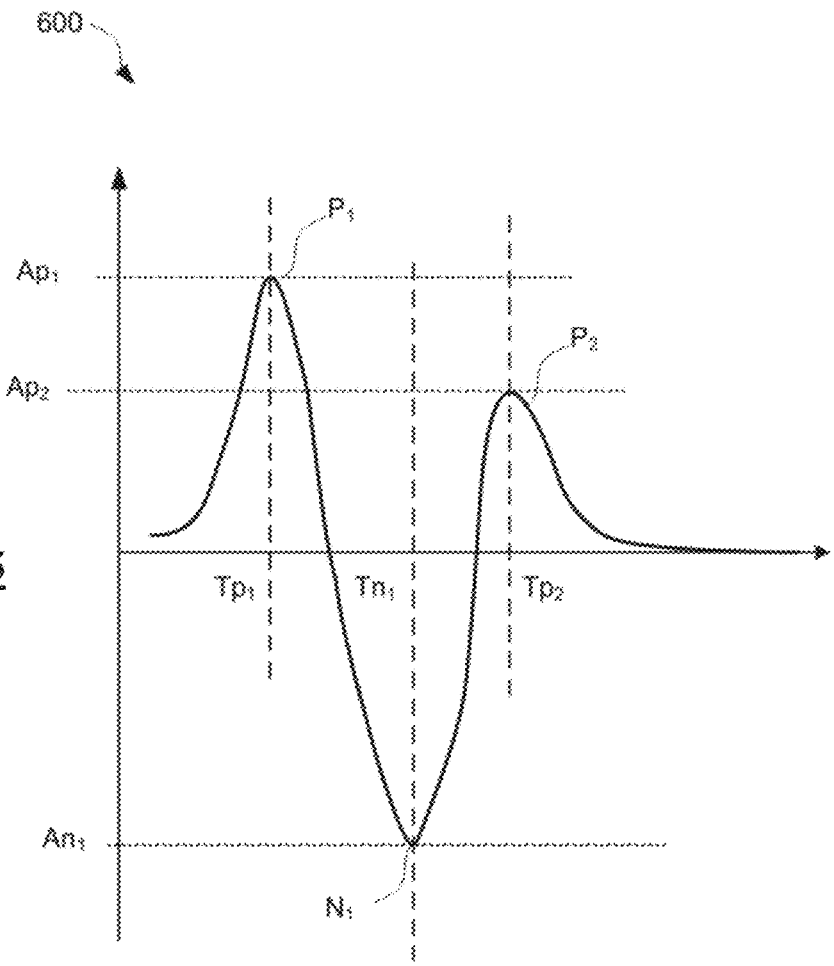
FIG. 5 illustrates the typical form of an electrically evoked compound action potential (ECAP) of a healthy subject.

FIG. 5 illustrates the typical form 600 of an ECAP of a healthy subject, as recorded at a single electrode referenced to the system ground 130. The shape and duration of the ECAP 600 shown in FIG. 5 is predictable because it is a result of the ion currents produced by the ensemble of fibres depolarising and generating action potentials (APs) in response to stimulation. The evoked action potentials (EAPs) generated synchronously among a large number of fibres sum to form the ECAP 600. The conduction velocity of the AP on each fibre is determined largely by the diameter of that fibre. The ECAP 600 generated from the synchronous depolarisation of a group of similar fibres comprises a positive peak P1, then a negative peak N1, followed by a second positive peak P2. This shape is caused by the region of activation passing the measurement electrode as the action potentials propagate along the individual fibres.

The ECAP may be recorded differentially using two measurement electrodes, as illustrated in FIG. 3. Depending on the polarity of recording, a differentially recorded ECAP may take an inverse form to that shown in FIG. 5, i.e. a form having two negative peaks N1 and N2, and one positive peak P1.

The ECAP 600 may be parametrised by any suitable parameter(s) of which some are indicated in FIG. 5. The amplitude of the positive peak P1 is $Ap_1$ and occurs at time $Tp_1$. The amplitude of the positive peak P2 is $Ap_2$ and occurs at time $Tp_2$. The amplitude of the negative peak P1 is $|An_1|$ and occurs at time $Tn_1$. The peak-to-peak amplitude is $Ap_1$-$An_1$. A recorded ECAP will typically have a maximum peak-to-peak amplitude in the range of microvolts and a duration of 2 to 3 ms.

The stimulator 100 is further configured to sense the existence and intensity of ECAPs 170 propagating along nerve 180, whether such ECAPs are evoked by the stimulus from electrodes 2 and 4, or otherwise evoked. To this end, any electrodes of the array 150 may be selected by the electrode selection module 126 to serve as measurement electrode 6 and measurement reference electrode 8, whereby the electrode selection module 126 selectively connects the chosen electrodes to the inputs of the measurement circuitry 128. Thus, signals sensed by the measurement electrodes 6 and 8 are passed to the measurement circuitry 128, which may comprise an amplifier and an analog-to-digital converter (ADC). The measurement circuitry 128 for example may operate in accordance with the teachings of the above-mentioned International Patent Application Publication No. WO2012/155183.

Neural responses obtained from the measurement electrodes 6, 8 via measurement circuitry 128 are processed by controller 116 to obtain information regarding the effect of the applied stimulus upon the nerve 180. In some implementations, neural responses are processed by controller 116 in a manner which extracts and stores one or more parameters from each response or group of responses. In one such implementation, the parameter comprises a peak-to-peak ECAP amplitude in microvolts (µV). For example, the neural responses may be processed to determine the peak-to-peak ECAP amplitude in accordance with the teachings of International Patent Publication No. WO2015/074121, the contents of which are incorporated herein by reference. Alternative implementations may extract and store an alternative parameter from the response to be stored, or may extract and store two or more parameters from the response.

Stimulator 100 applies stimuli over a potentially long period such as days, weeks, or months and during this time may store parameters of neural responses, stimulation settings, paraesthesia target level, and other operational parameters in memory 118. To effect suitable SCS therapy, stimulator 100 may deliver tens, hundreds or even thousands of stimuli per second, for many hours each day. Each neural response or group of responses generates one or more parameters such as a measure of the amplitude of the neural response. Stimulator 100 thus may produce such data at a rate of tens or hundreds of Hz, or even kHz, and over the course of hours or days this process results in large amounts of clinical data which may be stored in the clinical data store 120 of memory 118. Memory 118 is however necessarily of limited capacity and care is thus required to select compact data forms for storage into the memory 118, to ensure that the memory 118 is not exhausted before such time that the data is expected to be retrieved wirelessly by external device 192, which may occur only once or twice a day, or less.

In some implementations, the electronics module 110 is not configured to be implanted along with the electrode array 150. Instead, the electronics module 110 is configured to be located outside the body while still being connectable to the electrode array 150. Otherwise, such an electronics module 110 is the same as previously described. Such a non-implantable electronics module may be used temporarily for trial purposes to determine the efficacy of the therapy for a particular patient. A stimulator 100 comprising a non-implantable electronics module 110 and an implantable electrode array 150 may still be referred to as an implantable stimulator or an implantable device. The description that follows applies to implantable devices comprising implantable or non-implantable electronics modules.

A CLNS device comprises a stimulator that takes a stimulus intensity value and converts it into a neural stimulus comprising a sequence of electrical pulses according to a predefined stimulation pattern. The stimulation pattern is characterised by multiple parameters including stimulus intensity (amplitude), pulse width, number of phases, order of phases, number of stimulus electrode poles (two for bipolar, three for tripolar etc.), and stimulus rate or frequency. At least one of the stimulus parameters, usually the stimulus intensity, is controlled by the feedback loop.

In an example CLNS device, a user (e.g. the patient or a clinician) sets a target neural response value, and the CLNS device performs proportional-integral-differential (PID) control. In some implementations, the differential contribution is disregarded and the CLNS device uses a first order integrating feedback loop. The stimulator produces stimulus in accordance with a stimulus intensity parameter, which evokes a neural response in the patient. The evoked neural response (e.g. an EC AP) is detected and its amplitude measured by the CLNS device and compared to the target neural response value.

The measured neural response amplitude, and its deviation from the target neural response value, is used by the feedback loop to determine possible adjustments to the stimulus intensity parameter to maintain the neural response at the target value. If the target value is properly chosen, the patient receives consistently comfortable and therapeutic stimulation through posture changes and other perturbations to the stimulus/response behaviour.

Figure 4:
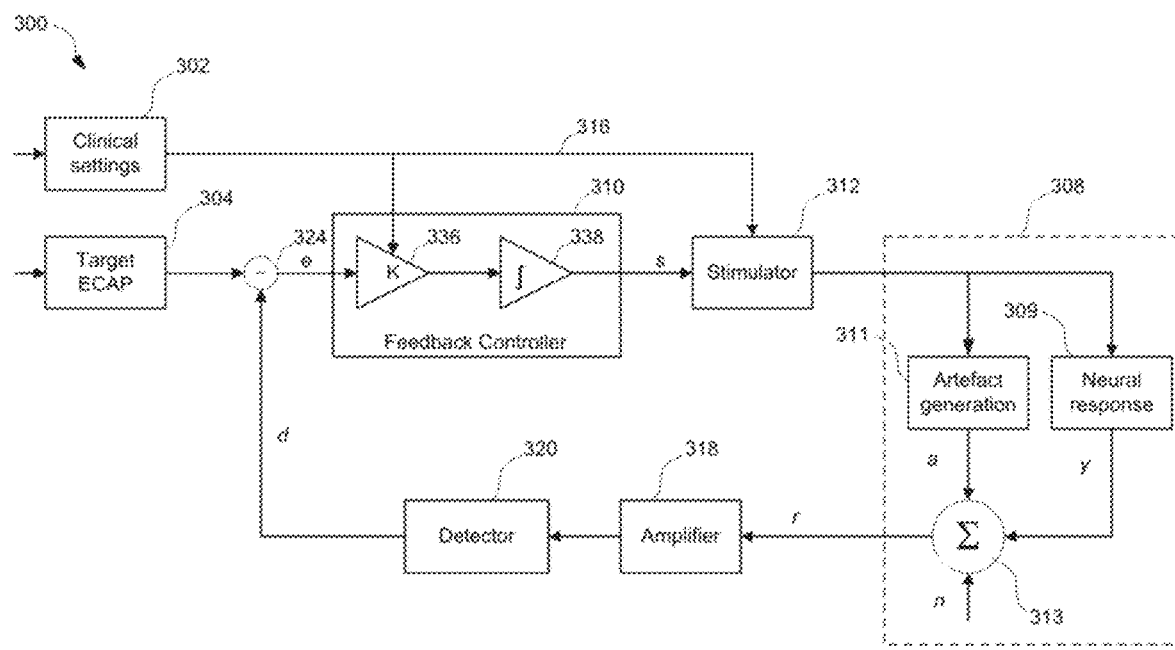
FIG. 4 is a schematic illustrating elements and inputs of a closed loop neurostimulation system, according to one implementation of the present technology.

FIG. 4 is a schematic illustrating elements and inputs of a closed loop neurostimulation (CLNS) system 300, according to one implementation of the present technology. The system 300 comprises a stimulator 312 which converts a stimulus intensity parameter (for example a stimulus current value) s, in accordance with a set of predefined stimulus parameters, to a neural stimulus comprising a sequence of electrical pulses on the stimulus electrodes (not shown in FIG. 4). According to one implementation, the predefined stimulus parameters comprise the number and order of phases, the number of stimulus electrode poles, the pulse width, and the stimulus rate or frequency.

The generated stimulus crosses from the electrodes to the spinal cord, which is represented in FIG. 4 by the dashed box 308. The box 309 represents the evocation of a neural response y by the stimulus as described above. The box 311 represents the evocation of an artefact signal a, which is dependent on stimulus intensity and other stimulus parameters, as well as the electrical environment of the measurement electrode. Artefact is described in more detail in the above-mentioned International Patent Publication No. WO2020/082126. Various sources of noise n may add to the evoked response y at the summing element 313 before the evoked response is measured, including electrical noise from external sources such as 50 Hz mains power; electrical disturbances produced by the body such as neural responses evoked not by the device but by other causes such as peripheral sensory input, EEG, EMG; and electrical noise from amplifier 318.

The neural recruitment arising from the stimulus is affected by mechanical changes, including posture changes, walking, breathing, heartbeat and so on. Mechanical changes may cause impedance changes, or changes in the distance and orientation of the nerve fibres relative to the electrode lead(s). As described above, the intensity of the evoked response provides a measure of the recruitment of the fibres being stimulated. In general, the more intense the stimulus, the more recruitment and the more intense the evoked response. An evoked response typically has a maximum amplitude in the range of microvolts, whereas the applied stimulus to evoke the response is typically several volts.

The total response signal r (including evoked neural response, artefact, and noise) is amplified by the signal amplifier 318 and then measured by the detector 320. The detector 320 outputs a measured response intensity d. In one implementation, the neural response intensity comprises an ECAP value. The comparator 324 compares the measured response intensity d to the target ECAP value as set by the target ECAP controller 304 and provides an indication of the difference between the measured response intensity d and the target ECAP value. This difference is the error value, e. The error value e is input into the feedback controller 310.

The feedback controller 310 calculates an adjusted stimulus intensity parameter, s, with the aim of maintaining a measured response intensity d equal to the target ECAP value. Accordingly, the feedback controller 310 adjusts the stimulus intensity parameter s to minimise the error value, e. In one implementation, the controller 310 utilises a first order integrating function, using a gain element 336 and an integrator 338, in order to provide suitable adjustment to the stimulus intensity parameter s. According to such an implementation, an adjustment δs to the current stimulus intensity parameter s may be computed by the feedback controller 310 as $$\delta s = Ke \quad (1)$$

A target ECAP value is input to the comparator 324 via the target ECAP controller 304. In one embodiment, the target ECAP controller 304 provides an indication of a specific target ECAP value. In another embodiment, the target ECAP controller 304 provides an indication to increase or to decrease the present target ECAP value. The target ECAP controller 304 may comprise an input into the neural stimulus device, via which the patient or clinician can input a target ECAP value, or indication thereof. The target ECAP controller 304 may comprise memory in which the target ECAP value is stored, and provided to the comparator 324.

A clinical settings controller 302 provides clinical parameters to the system, including the gain K for the gain controller 336 and the stimulation parameters for the stimulator 312. The clinical settings controller 302 may be configured to adjust the gain value, K, of the gain controller 336 to adapt the feedback loop to patient sensitivity. The clinical settings controller 302 may comprise an input into the neural stimulus device, via which the patient or clinician can adjust the clinical settings. The clinical settings controller 302 may comprise memory in which the clinical settings are stored, and are provided to components of the system 300.

In some implementations, two clocks (not shown) are used, being a stimulus clock operating at the stimulus frequency (e.g. 60 Hz) and a sample clock for sampling the measured response r (for example, operating at 10 kHz). As the detector 320 is linear, only the stimulus clock affects the dynamics of the CLNS system 300. On the next stimulus clock cycle, the stimulator 312 outputs a stimulus in accordance with the adjusted stimulus intensity s. Accordingly, there is a delay of one stimulus clock cycle before the stimulus is updated in light of the error value e. Alternative embodiments may have a delay of less than one stimulus clock cycle if utilising intra-stimulus recruitment control, for example in accordance with the teachings of International Patent Publication No. WO2022/170388, the content of which is incorporated herein by reference.

A key design goal of an automated lead offset measurement program is to allow automated measurement of the relative rostra-caudal position (rostro-caudal offset) of implanted percutaneous electrode leads in patients prior to system programming. This helps to inform programming of the system by the programming clinician via the CPA. The foundational premise of the measurement is that the position of the stimulating electrode(s) on one lead can be inferred from the effect of stimuli from those electrodes on a measurement taken on the adjacent lead.

Figure 6:
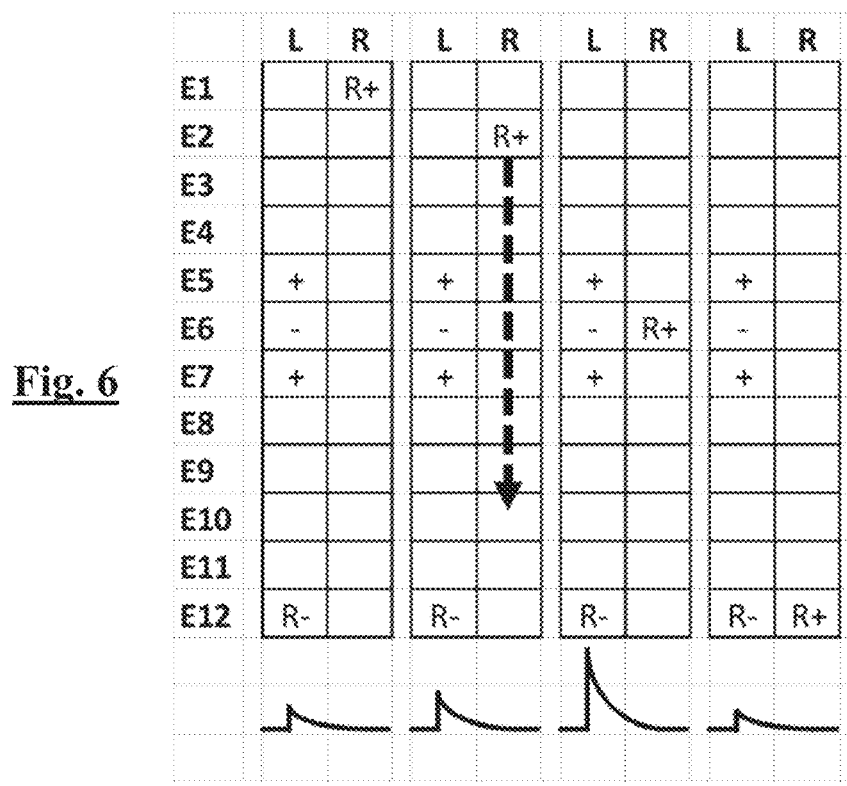
FIG. 6 illustrates a process of automated lead offset measurement in accordance with one embodiment of the invention.

To this end, FIG. 6 illustrates the premise of the Automated Lead Offset Measurement. The diagram shows a set of two 12-electrode leads. L and R denote left lead and right lead and the labels E1-E12 denote the 12 electrodes on each lead. The four sets of leads, left to right, represent the progression of time as the Lead Offset Measurement is performed. The + and − symbols on electrodes 5, 6, 7 on the left lead denote the positive and negative stimulating electrodes, R− denotes the measurement reference electrode. R+ denotes the measurement (a.k.a. recording) electrode. The automated lead offset measurement algorithm progresses the recording electrode down the length of the R lead, acquiring a signal or set of signals at each position. The performance of the lead offset measurement is premised on the idea that the proximity of the recording electrode to the stimulating electrodes causes an identifiable change in the signals acquired at each position on the R lead. This change is illustrated in the simulated artefact waveforms below each set of leads. As illustrated, the artefact when the recording electrode is electrode 6 on the right lead is significantly larger than the artefact of the other sets of leads.

The present embodiment in particular recognises that signals arising due to stimulation artefact can be acquired by the system during this lead offset automation which allow for reliable measurement of the rostro-caudal lead offset and has characteristics which allow inference of the position of the stimulating electrodes.

Figure 7:
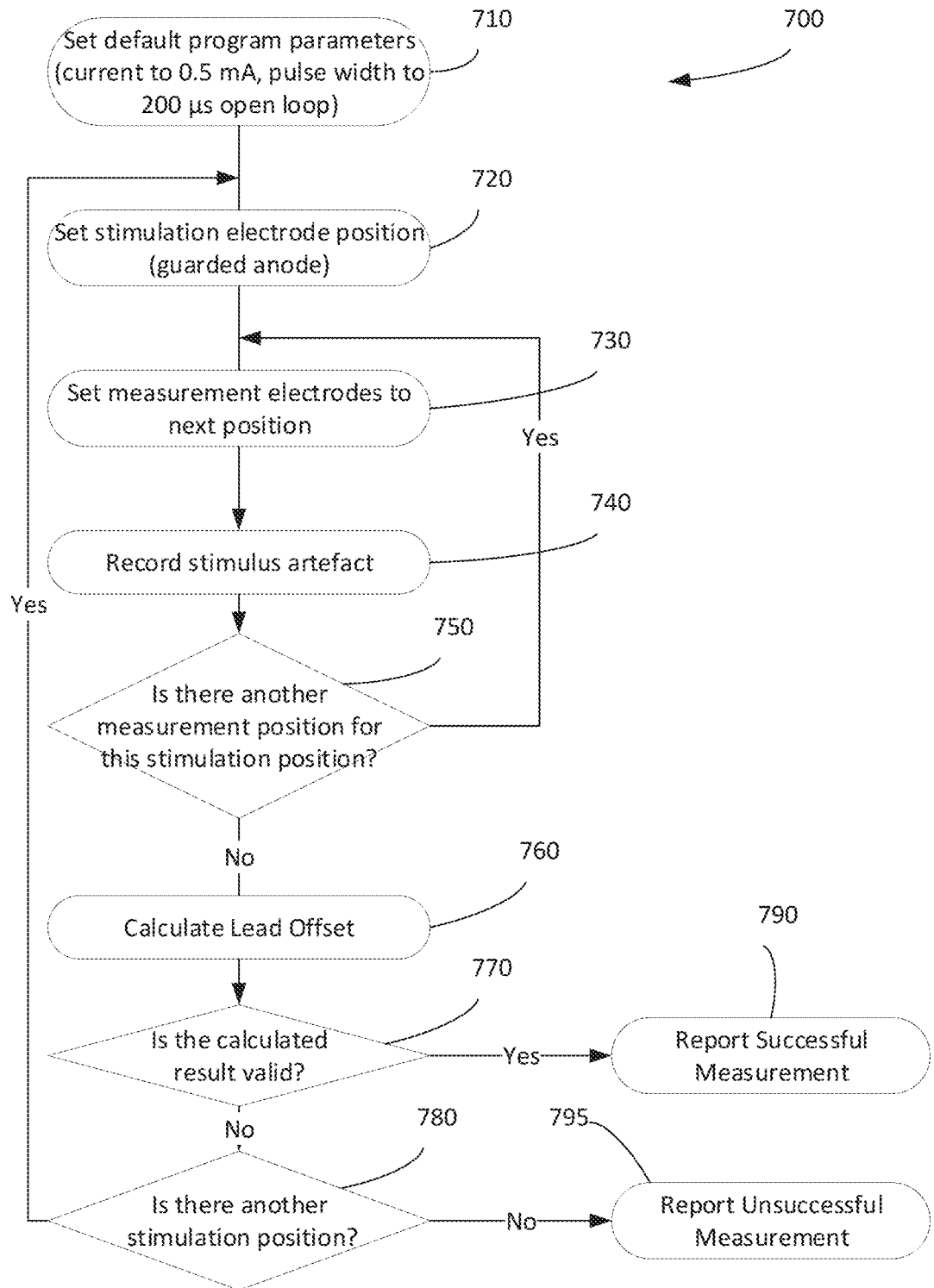
FIG. 7 is a flowchart of the lead offset automation workflow carried out by the clinical programming application according to one embodiment of the present technology.

FIG. 7 illustrates the lead offset automation workflow carried out by the CPA according to one embodiment of the present technology. The workflow 700 starts at step 710, at which the CPA configures the stimulator with default therapy parameters, such as a stimulus current of 0.5 mA, and a stimulus pulse width of 200 μs. Step 710 also configures the stimulator to operate in open loop mode.

Step 720 configures the stimulator with a first stimulation electrode position and an electrode configuration that is suitable for lead offset estimation, such as a closely spaced shielded tripolar anode configuration (described below). Step 730 configures the stimulator with measurement electrodes in the next position at Which artefact is to be measured. Step 740 then delivers a stimulus via the stimulus electrodes, and measures and records the magnitude of the resulting stimulus artefact via the measurement electrodes. Step 750 then tests whether there is another measurement electrode position at which artefact is to be measured. If so ("Yes"), the workflow 700 returns to step 730. If not ("No"), step 760 calculates lead offset from the recorded artefact magnitudes at the respective measurement electrode positions in the manner described below. Step 770 then tests the validity of the calculated result according to criteria described below. If the calculated result is valid ("Yes"), the calculated result is reported to the user of the CPA at step 790, and the workflow concludes. If not ("No"), step 780 tests whether there is another position for stimulus electrodes that could be used for the calculation. If so ("Yes"), the CPA returns to step 720 to repeat steps 720 to 790 in respect of that new position for the stimulus electrodes. Otherwise ("No"), the CPA reports to the user that the offset measurement was unsuccessful at step 795, and the workflow 700 concludes.

Figure 8:
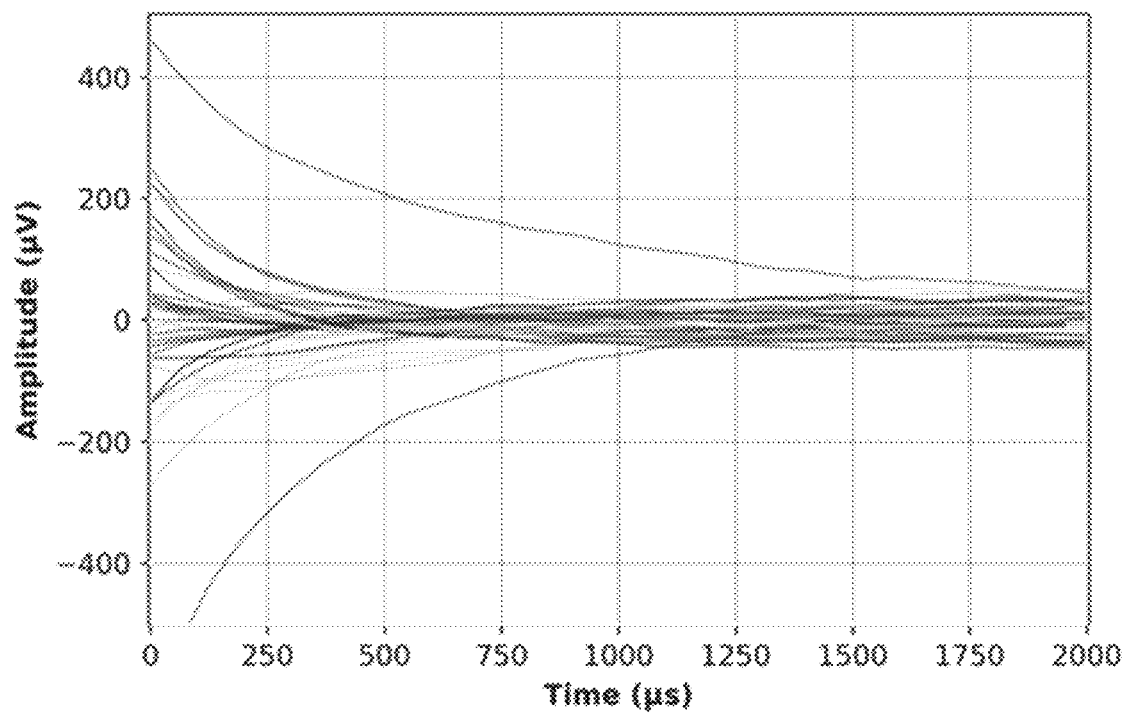
FIG. 8 is a plot illustrating example artefact signals recorded by an example SCS system in clinical practice.

FIG. 8 illustrates example artefact signals recorded by an example SCS System in clinical practice. The present invention recognises that the strength of such signals, whether measured as amplitude, power, energy under the curve, or the like, depends in part upon the rostro-caudal offset between the two leads used for stimulation and recording respectively. The strength of such signals may be measured as a peak artefact magnitude observed following completion of the stimulus, for example in the period of 0-1000 μs post-stimulus.

The stimulation paradigm may be selected in order to generate suitable stimulus artefacts which would allow for and facilitate measurement of the lead offset. This selection recognises that configuration of the stimulating electrodes and the stimulation pulses during lead offset measurement defines the electric field driving the generation of the artefact used to measure the lead offset.

Figure 9:
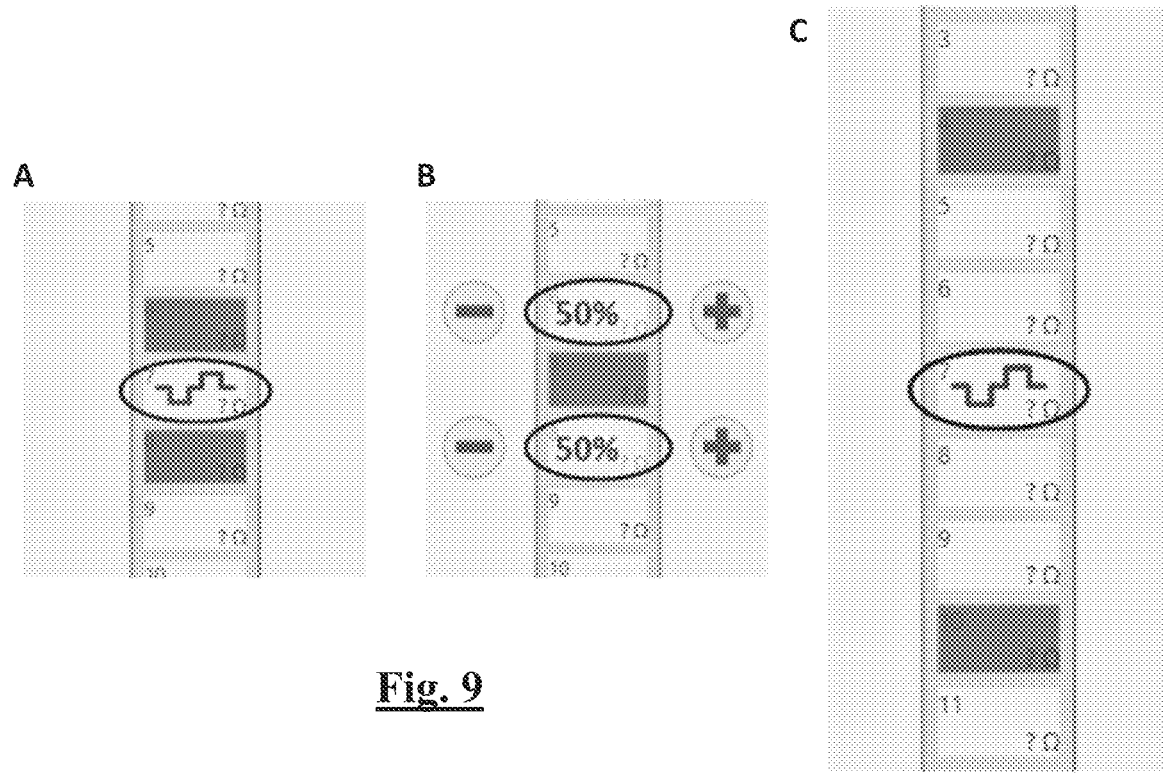
FIG. 9 illustrates a number of candidate stimulus electrode configurations.

A preferred characteristic of the stimulus electrode configuration is one that restricts artefact generation to spatially occur within a small proximity of the stimulating electrodes. There are numerous candidate stimulus electrode configurations, of which three are depicted in FIG. 9, namely a shielded cathode tripolar stimulus electrode configuration (labelled as A), a shielded anode tripolar stimulus electrode configuration (labelled as B) and a spaced shielded anode tripolar stimulus electrode configuration (labelled as C).

Additionally, the stimulus phase configuration may be selected in order to facilitate the generation of stimulus artefact so that it can be used for lead offset determinations. In this regard, as the lead offset measurement is intended to utilise artefact magnitude as a key measurement, deliberately generating artefact in the recorded signal is desirable. Thus, a lead offset measurement automation process may be equipped with a biphasic, triphasic or other stimulus phase configuration which is configured to generate larger and more easily detected artefact signals that allow for and facilitate lead offset measurement.

Results indicate that the artefact magnitude recorded in close proximity to the stimulating electrode is substantially higher, i.e. better for lead offset measurement, when using biphasic rather than triphasic stimulation pulses. Thus, utilisation of biphasic pulses as part of a stimulation paradigm for lead offset measurement may be advantageous in embodiments of the invention.

Alternative embodiments may nevertheless utilise triphasic stimulation, when suitably configured. In particular, the stimulus phase configuration may comprise a triphasic stimulus in which a ratio of charge of a first phase relative to a third phase is adjusted so as to maximise or increase stimulus artefact. As shown for example in FIGS. 8 and 9 of International Publication No. WO2017/219096, the content of which is incorporated herein by reference, such adjustment of the ratio of charge of a first phase relative to a third phase provides some control over the resultant artefact. In contrast to the goal of WO2017/219096, which is to use such adjustments to minimise artefact, embodiments of the present invention may instead use such adjustments to increase or maximise artefact so as to improve measurement sensitivity of the lead offset measurements based on stimulus artefact. In another alternative, monophasic stimulation may be utilised to create large stimulus artefact, with charge recovery effected for example by passive grounding of a case electrode and/or by delivering a charge recovery pulse after completion of the lead offset measurement.

Further, a lead offset measurement process preferably utilises a stimulus electrode configuration which will not only facilitate generation of artefact of a larger amplitude, but will also create a spatially constrained artefact signal that could be better used for optimised offset measurement. Results indicate that a closely spaced shielded anode tripolar stimulus electrode configuration (FIG. 9, labelled B) demonstrates good localisation of artefact in close proximity to the stimulation site, allowing for reliable measurement of the actual lead offset.

It is further noted that offset measurement is most effective when the stimulation site has the maximum possible number of recording sites available both proximal and distal to it. In other words, measurement is most effective when the stimulation site facilitates recording on the largest amount of overlapping sections of lead.

Turning from the preceding considerations as to suitable selection of stimulus phase configuration and stimulus electrode configuration, consideration is now given to suitable models to determine lead offset using artefact from the recordings. The recorded artefacts may be analysed to determine what the lead offset is. In order to do this, it is necessary to identify characteristics of the signal which are sensitive to proximity with the stimulus electrode, and fit the observation of the characteristic to an expected model which enables inference of the lead offset. The following discusses two such characteristics, with associated models, which enable lead offset measurement using artefact.

Figure 10:
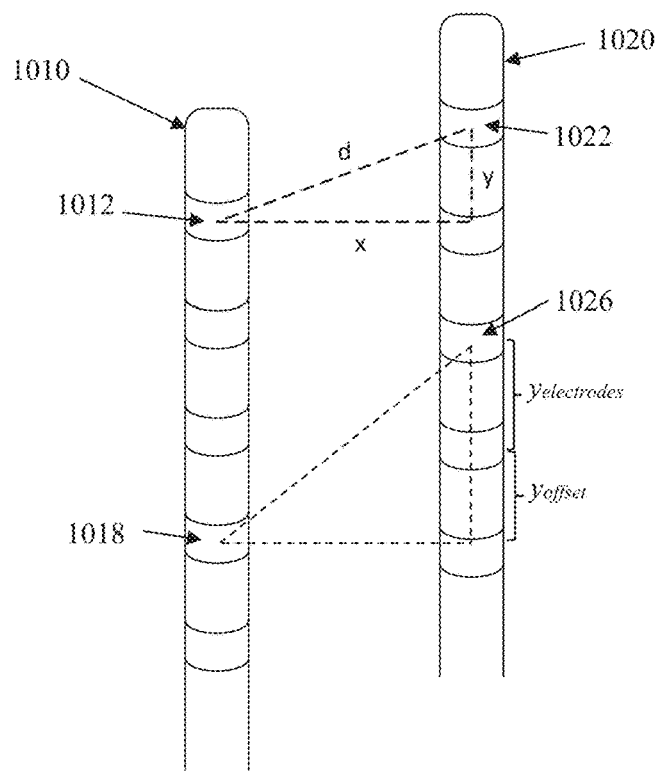
FIG. 10 illustrates the geometrical context for development of a distance squared model of lead offset.

With reference to FIG. 10, a distance-squared model is developed, noting that the distance from a stimulus electrode 1012 upon a first electrode lead 1010 to a recording electrode 1022 on the opposite lead 1020 is:

$$d=\sqrt{x^2+y^2},$$

where x is the distance between the leads 1010 and 1020 (assumed to be parallel) and y is the vertical distance between the stimulus electrode and the recording electrode. In the example of FIG. 10, when considering electrodes 1012 and 1022 which occupy equivalent positions on each respective lead (in this case being the most distal position of each lead), the vertical distance y is the (unknown) lead offset. More generally, when considering electrodes which do not occupy equivalent positions on each respective lead, such as electrodes 1018 and 1026 for example, the vertical distance y is the (unknown) lead offset $y_{offset}$ plus the fixed pre-existing vertical distance $y_{electrodes}$ between the non-equivalent positions of the stimulating electrode 1018 and measurement electrode 1026, the latter of which exists even when the leads are parallel with no offset. In such cases it is noted that the lead offset measure of interest, $y_{offset}$, can still be estimated by noting that:

$$y=y_{electrodes}+y_{offset}$$

with $y_{electrodes}$ either being zero when considering electrodes which occupy equivalent positions on each respective lead, or being known a priori from the lead design when considering electrodes which do not occupy equivalent positions on each respective lead.

We assume a model of artefact where the peak-to-peak magnitude of the artefact decreases proportionately with distance squared:

$$A \propto \frac{1}{d^2}$$

Figure 11:
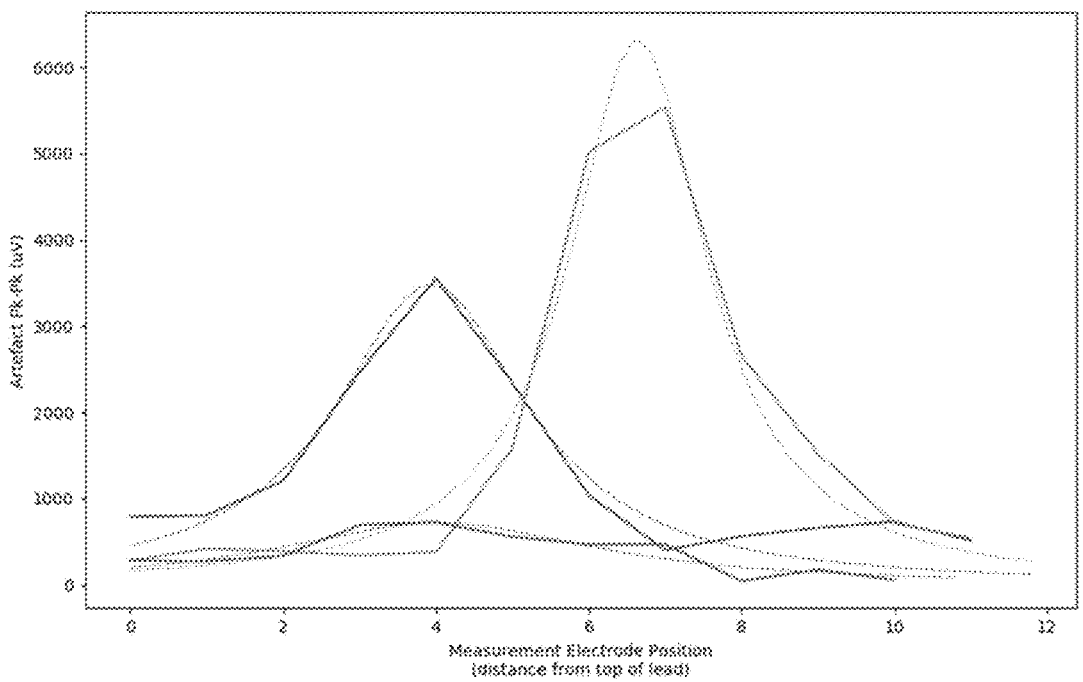
FIG. 11 is a plot of recordings of artefact vs. measurement electrode position.

The model was developed by taking numerous artefact measurements at different measurement electrode positions in a saline bath. Three of these curves are shown in FIG. 11, which shows three recordings of artefact vs. measurement electrode position taken in a saline bath. The dashed lines show the curves fitted to the artefact-distance model. A more detailed model was developed from these curves:

$$A(d) = \frac{a}{(d-b)^2 + c^2}$$

where d is the nominal distance from the stimulus electrode to the measurement electrode. The lead offset is calculated by fitting the recorded data points of artefact vs. distance to the model equation, A(d), to obtain the optimum fitted parameters, a, b and c. The lead offset will be the value of b.

Initial Fitting Conditions can also be used. The fitting algorithm can be provided with starting values of a, b and c, which can help to fit the curve faster. The initial values are: a=1; b=the distance of the data point with the maximum artefact level; and c=0.

Result Validation can also be implemented. Here, the fitted curve is marked as invalid if any of the following are true:
   The curve fitting algorithm is not able to converge in the allocated maximum number of iterations (set to default value of 50000 iterations)
   a≤0—this implies that the curve of A(d) is upside-down, which suggests that the data is too noisy to fit properly
   The peak is outside the range of the electrodes
   The ratio between the peak of the fitted curve and the peak of the raw points is less than 0.8 or greater than 1.2 (i.e. the curve was not accurately fitted to the raw points)
   The ratio between the height of the fitted curve and the mean of the raw points is less than 3 (i.e. the peak isn't high enough to warrant an accurate measurement)

If the curve is invalid, the initial lead offset estimate is returned, which will be a multiple of the electrode spacing (7 mm) and is calculated by finding the maximum value of the data points.

Figure 12:
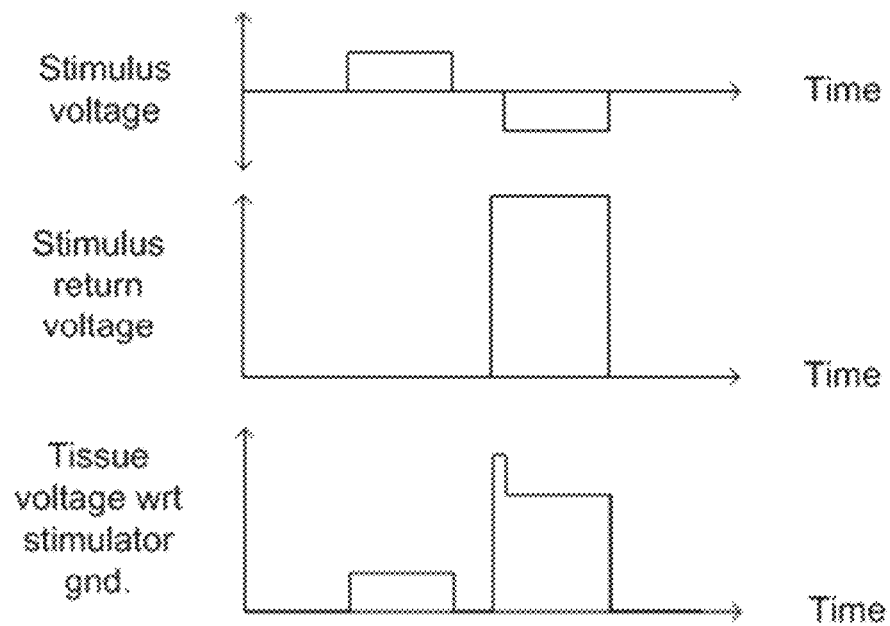
FIG. 12 illustrates tissue voltage in response to a biphasic pulse.

A second model is also now presented. Based on the results of simulation and saline based investigations, the stimulation artefact which is recorded at the implanted measurement electrodes is thought to be an aggregate of component signals which are generated by steps in the tissue voltage in response to charge delivered to the implanted stimulating electrodes. Charge is typically delivered to a combination of implanted stimulating and return electrodes. The stimulating electrode voltages are alternated between poles of the stimulation current source(s), whilst the return electrode voltages are alternated between the stimulator reference and supply voltages. The tissue voltage is the sum of the stimulating electrode voltages and the return electrode voltage. FIG. 12 illustrates tissue voltage (bottom) in response to a biphasic pulse delivered on the stimulating electrodes (top) and return electrodes (middle). The small peak in the tissue voltage at the start of the second phase is a result of "pre-loading" in which the return electrode is connected to the supply voltage slightly earlier, for example 12 microseconds earlier, than the stimulus electrode is connected to the stimulation current source.

For each voltage step generated by the stimulus and return electrodes, two time-varying voltage response components are seen at the electrode-tissue interface.

The electrode-tissue interface is the interface between the aqueous, ion-rich environment of the human body and the charged metal lattice of an implanted electrode. In real terms, the aqueous ions display unique behaviours in response to rapid charging and discharging of the metal lattice, principally characterised by the rapid formation and diffusion of a bilayer of ions on the electrode surface. This is known as the ionic double layer and it has both capacitive and resistive characteristics. The aggregation and diffusion of ions from the metal surface is purely capacitive in an ideal system. However, a reversible modification of ionic species and exchange of electrodes at the metal surface is also known to occur with a voltage-dependent rate. As such the electrode-tissue interface may be electrically characterised using a concept known as the Constant Phase Element (CPE), which is effectively a leaky capacitor.

The voltage response of a CPE to a tissue voltage step can be described with two component voltage signals which have the properties of a fractional pole. The determination of these components is described for example in international Patent Publication Nos. WO2020/124135 and WO2020/082126 by the present applicant. Each of these time-varying components represents one of the distinct capacitive and resistive behaviours of the CPE. One component has a positive slope and is representative of the capacitive or fast response of the tissue voltage. We term this the step component:

$$s(t) = k_s \frac{1}{1-\alpha} t^{1-\alpha}$$

The other time-varying component has a negative slope and represents the resistive or slow behaviour of the tissue voltage as the CPE relaxes. We term this the impulse component:

$$i(t) = k_i t^{-\alpha}$$

The time constant $\alpha$ for the fractional poles is thought to be dependent on the geometry of the electrode-tissue interface and for the example SCS System a constant value may be used:

$$\alpha = 0.364$$

The scalar multipliers for the step ($N_s$) and impulse ($k_i$) components are assumed to be dependent on the amplitude of stimulation current delivered to the stimulating electrodes and the characteristics of tissue between stimulation and recording sites.

For a given biphasic or triphasic stimulus phase configuration, the stimulation and return voltage waveforms will contain multiple steps. Each edge of a voltage step acts as a singularity at which an independent set of step and impulse components may be defined. The number and timing of these edges/singularities can be exactly defined based on the stimulation waveform and depend on the following adjustable parameters of the system: Number of Phases (Biphasic or Triphasic); Polarity of the First Phase (Negative or Positive); Pulse Width; Interphase Gap.

Figure 13:
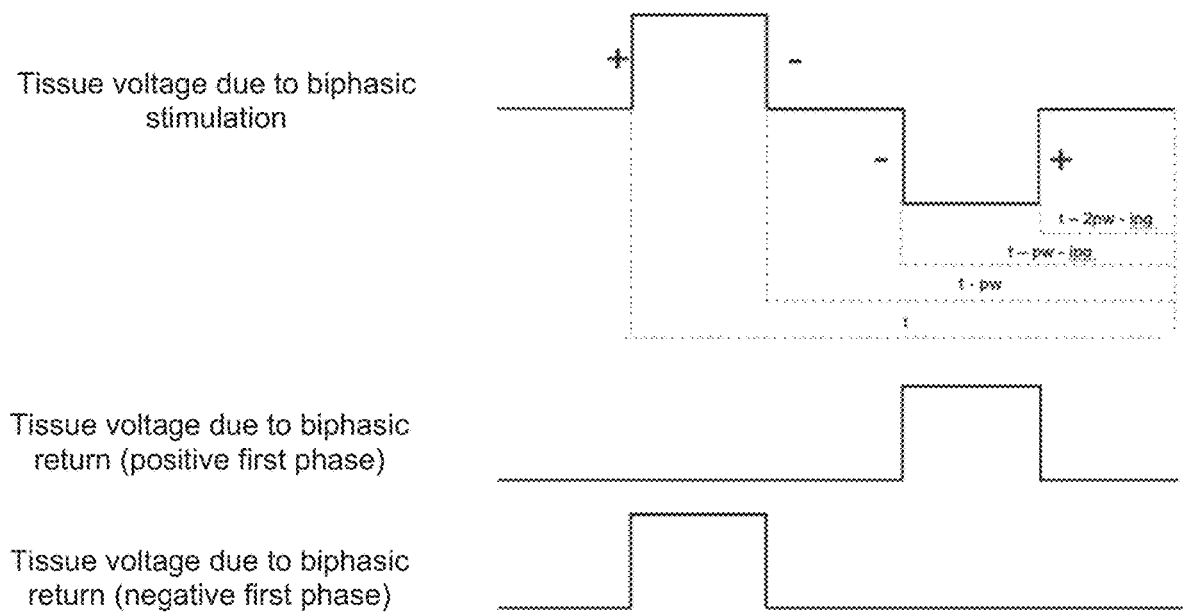
FIG. 13 shows voltage waveforms for stimulation and return electrodes during either a biphasic pulse with a positive first phase, or a biphasic pulse with a negative first phase.
Figure 14:
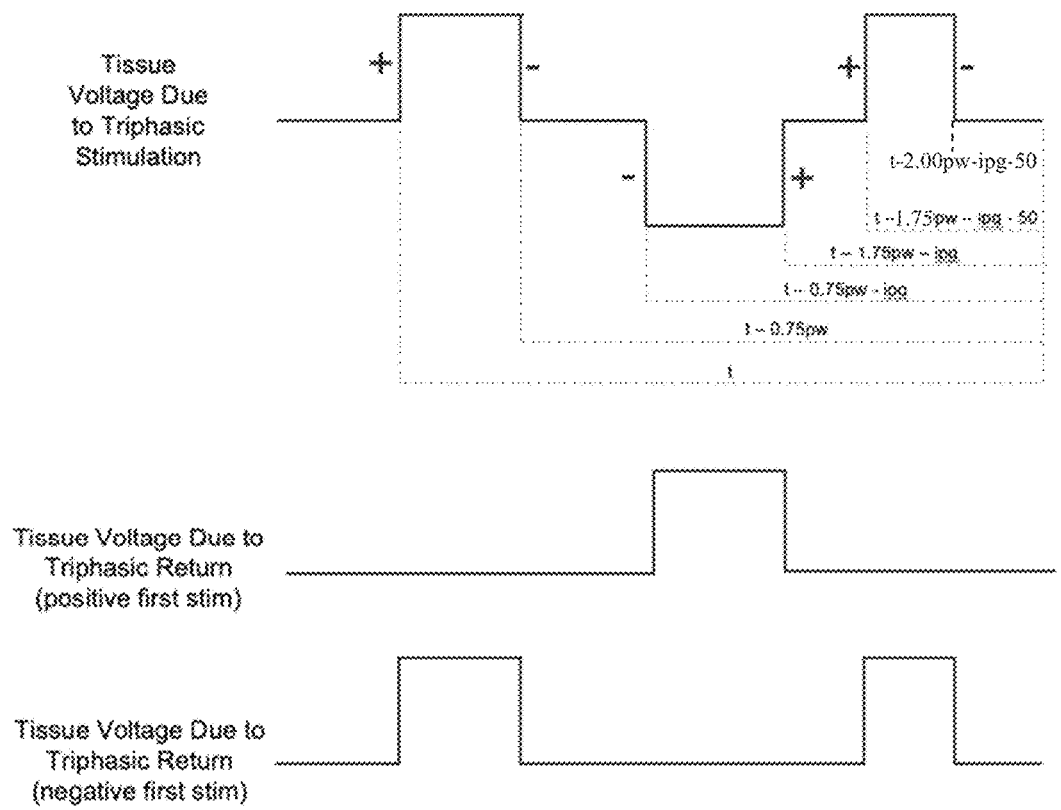
FIG. 14 shows voltage waveforms for the stimulation and return electrodes during two types of triphasic pulse.

The recorded artefact is the scaled sum of all of the time-offset step and impulse components generated by the stimulation and return voltage waveforms. General equations may be defined for these time-offset stimulation and return step and impulse components which use known parameters of the stimulation waveform. FIG. 13 shows voltage waveforms for the stimulation and return electrodes during two types of biphasic pulse: a biphasic pulse with a positive first phase (as in FIG. 12), and a biphasic pulse with a negative first phase. The exact timing of the step edges is specified relative to t, where t is the time at the first edge. FIG. 14 shows voltage waveforms for the stimulation and return electrodes during two types of triphasic pulse: a triphasic pulse with a positive first phase, and a triphasic pulse with a negative first phase. The exact timing of the step edges is specified relative to t, where t is the time at the first edge.

Table 1 sets out the general definitions for each of the four artefact component waveforms, where css=Current Source Step, csi=Current Source Impulse, rs=Return Step, ri=Return Impulse, for each of four types of stimulus waveform.

TABLE 1

Definitions of four artefact components for each type of stimulus waveform.

| | Biphasic |
|---|---|
| Positive-First | css = s(t) − s(t − pw) − s(t − pw − ipg) + s(t − 2pw − ipg)<br>csi = i(t) − i(t − pw) − i(t − pw − ipg) + i(t − 2pw − ipg)<br>rs = s(t − pw − ipg) − s(t − 2pw − ipg)<br>ri = i(t − pw − ipg) − i(t − 2pw − ipg) |
| Negative-First | css = −s(t) + s(t − pw) + s(t − pw − ipg) − s(t − 2pw − ipg)<br>csi = −i(t) + i(t − pw) + i(t − pw − ipg) − i(t − 2pw − ipg)<br>rs = s(t) − s(t − pw)<br>ri = i(t) − i(t − pw) |
| | Triphasic |
| Positive-First | css = s(t) − s(t − 0.75pw) − s(t − 0.75pw − ipg) + s(t − 1.75pw − ipg) + s(t − 1.75pw − ipg − 50E$^{-6}$) − s(t − 2pw − ipg − 50E$^{-6}$)<br>csi = i(t) − i(t − 0.75pw) − i(t − 0.75 − ipg) + i(t − 1.75pw − ipg) + i(t − 1.75pw − ipg −50E$^{-6}$) − i(t − 2pw − ipg − 50E$^{-6}$)<br>rs = s(t − 0.75pw − ipg + 12E$^{-6}$) − s(t − 1.75pw − ipg)<br>ri = i(t − 0.75pw − ipg + 12E$^{-6}$) − i(t − 1.75pw − ipg) |
| Negative-First | css = −s(t) + s(t − 0.75pw) + s(t − 0.75pw − ipg) − s(t − 1.75pw − ipg) − s(t − 1.75pw − ipg − 50E$^{-6}$) + s(t − 2pw − ipg − 50E$^{-6}$)<br>csi = −i(t) + i(t − 0.75pw) + i(t − 0.75pw − ipg) − i(t − 1.75pw − ipg) − i(t − 1.75pw − ipg − 50E$^{-6}$) + i(t − 2pw − ipg − 50E$^{-6}$)<br>rs = s(t + 12E$^{-6}$) − s(t − 0.75pw) + s(t − 1.75pw − ipg − 38E$^{-6}$) − s(t − 1.75pw − ipg − 50E$^{-6}$)<br>ri = i(t + 12E$^{-6}$) − i(t − 0.75pw) + i(t − 1.75pw − ipg − 38E$^{-6}$) − i(t − 1.75pw − ipg − 50E$^{-6}$) |

The preceding analysis thus provides elements sufficient to measure stimulation proximity using artefact components. The following section describes an implementation of the fractional-pole components model of artefact to enable lead offset measurement. The data used for this implementation was measured from human-implanted systems using a lead offset measurement feature.

As described above, the temporal characteristics of each of the four component signals which make up the recorded artefact may be defined as in Table 1 for each kind of stimulus waveform. However, each of these components will have some amplitude which is determined by uncontrolled factors such as tissue impedance. The amplitude for each for the four artefact components may be assigned an independent k value, such that:

$$y(t) = k_1 css(t) + k_2 csi(t) + k_3 rs(t) + k_4 ri(t)$$

where y(t) is the model for artefact.

These four artefact components describe slightly different component characteristics of the artefact, each of which will have a different sensitivity to the proximity of the stimulating electrodes. The premise of this method is that a staged fitting and recombination of the four component scalar values ($k_1$ through $k_4$) is able to reliably identify the measurement electrode which lies closest to the stimulating electrodes.

To achieve staged fitting of the four component scalar values ($k_1$ through $k_4$), for each set of artefacts acquired from each recording electrode during a measurement, the least-squares solution for $k_1$ through $k_4$ is determined for the following four-component model of artefact:

$$[k_1 k_2 k_3 k_4] \cdot [css(t) csi(t) rs(t) ri(t)] = Y$$

where Y is the average observed artefact for a given recording electrode.

The least-squares solution is then determined independently for each of the following four single-component models of artefact:

$$k_{1i} \cdot css(t) = Y$$

$$k_{2i} \cdot csi(t) = Y$$

$$k_{3i} \cdot rs(t) = Y$$

$$k_{4i} \cdot ri(t) = Y$$

where Y is the average observed artefact for a given recording electrode. The fitting therefore yields 8 scalars at each recording electrode.

Figure 15:
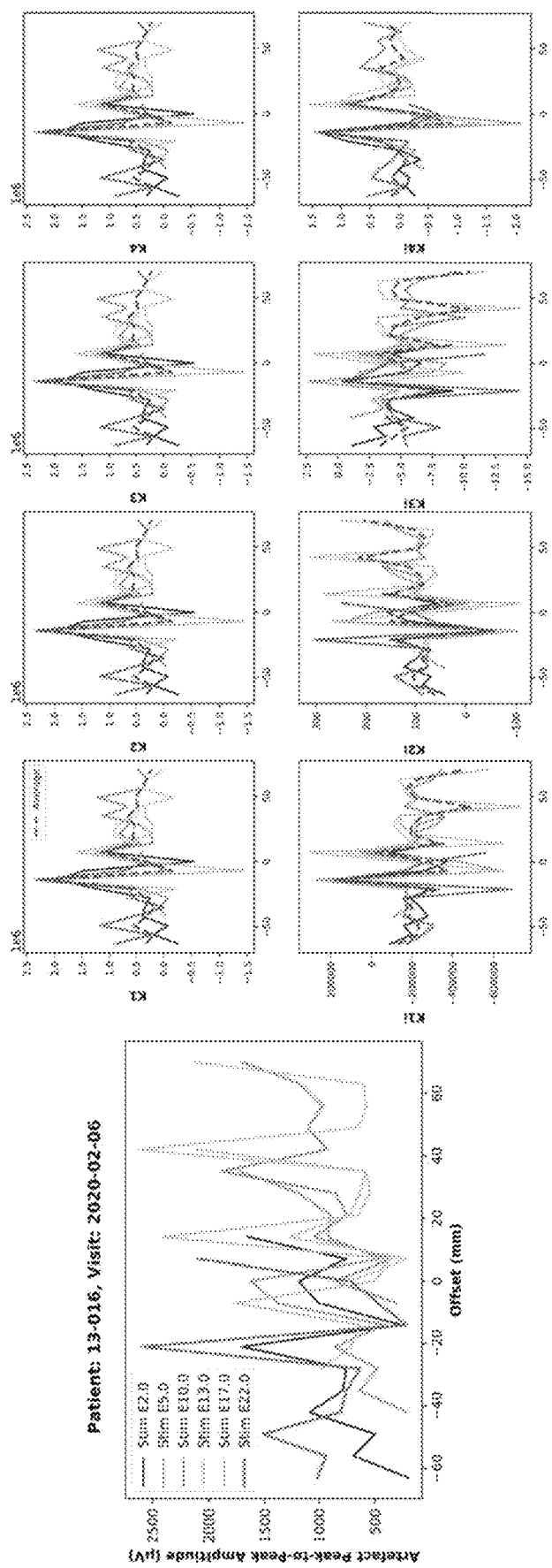
FIG. 15 shows fitted values for the 8 model scalars for artefacts measured in lead offset measurement, from a human patient.

FIG. 15 shows an example of the fitted values for the 8 scalars for artefacts measured in lead offset measurement from a human patient. Left panel: The peak-to-peak artefact amplitude (in µV) versus theoretical offset between the measurement and stimulation electrodes (in mm). Each line represents all of the measurements made at measurement electrodes across the lead adjacent to stimulation, for a particular set of stimulating electrodes. In this example, the measurement was repeated on six sets of stimulating electrodes. Right panel: The fitted values for $k_1$, $k_2$, $k_3$, $k_4$, $k_{1i}$, $k_{2i}$, $k_{3i}$, $k_{4i}$ for the set of measurements shown on the left.

Four aggregate scalars are then constructed which are used to generate four proposed solutions:

$$k_{1*4i} = k_1 k_{4i}$$

$$k_{2*4i} = k_2 k_{4i}$$

$$k_{2i*4i} = k_{2i} k_{4i}$$

$$k_{1i*2i} = k_{1i} k_{2i}$$

Figure 16:
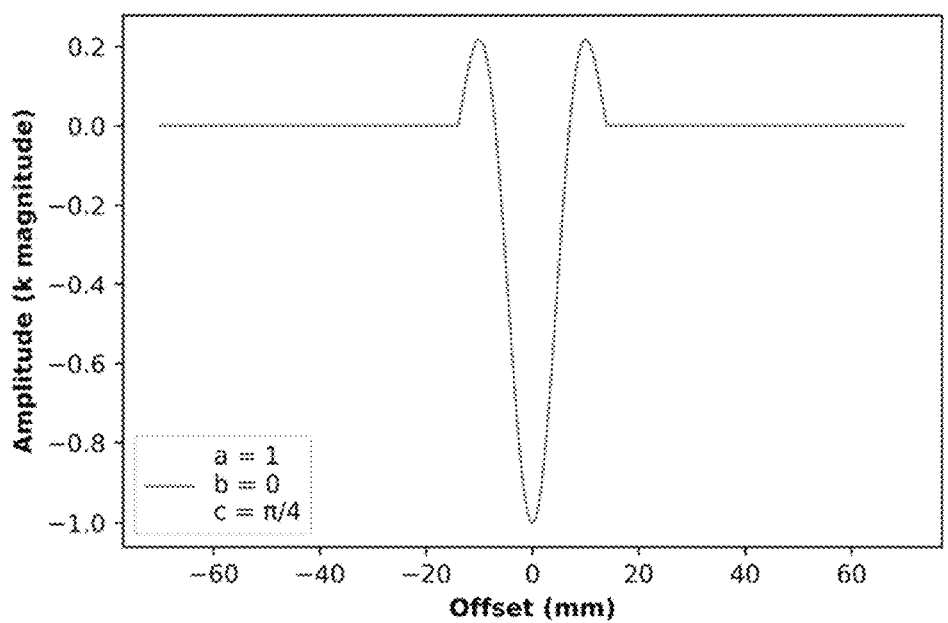
FIG. 16 shows the characteristic signal expected in the optimal solution of the model of FIG. 10.

Examples of the proposed solutions for the case shown in FIG. 15 are shown in FIG. 16 which shows an example of the characteristic signal expected in the optimal solution. This example is generated using the matched filter described below with parameters $a=1$, $b=0$ and $c=\pi/4$.

The characteristic signal that is expected in the solution is a large negative peak flanked by two smaller positive peaks. The position of the negative peak on the x-axis indicates the lead offset.

Figure 17:
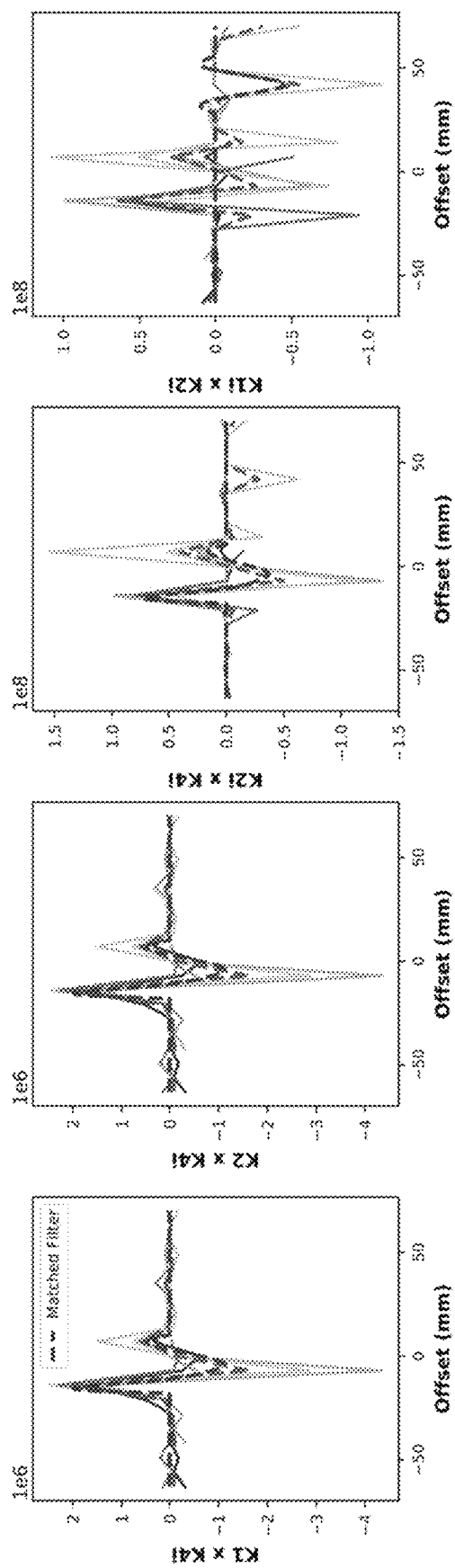
FIG. 17 shows an example of the four proposed solutions for the human data of FIG. 15.

This characteristic signal is apparent for $k_{1*4i}$, $k_{2*4i}$ and $k_{2i*4i}$ in FIG. 17 and indicates that the actual lead offset is approximately −7 mm. In particular, FIG. 17 shows an example of the four proposed solutions for the example shown above in FIG. 15. The dashed line shows the matched filter which allows automated measurement of the lead offset from each of the proposed solutions.

In turn, the present embodiments provide for design of a matched filter to automatically measure lead offset from a proposed solution. For each set of measurements, several of the four proposed solutions $k_{1*4i}$, $k_{2*4i}$, $k_{2i*4i}$, $k_{1i*2i}$ may show the characteristic signal. This is often obvious to a human observer. However, an automated method to identify the presence of the characteristic signal is necessary to enable an automated measurement of lead offset. To perform this task, a matched filter is used. The matched filter (F) is a model of the characteristic signal of interest (see FIG. 16) which has enough degrees of freedom to account for expected variation in the characteristic signal. The filter function takes three parameters a, b, c and operates on a vector x which is the offset axis in units of E where E is the offset in electrode spacings (for reference, all figures show the offset axis in mm which, for the 7 mm electrode spacings used, is equivalent to 7E).

The matched filter (F) is defined as follows:

$$F(x, a, b, c) = a \frac{\sin(x + b\pi)}{(x + b\pi)} \odot S(x, b) \odot H(x, a, b, c)$$

where $\odot$ denotes the Hadamard product; a is a scaling factor; b denotes the lead offset value in units of E; c is a skewing factor, which changes the relative weights of the three filter peaks; S is a square function centred at $-\pi b$:

$$S(x, b) = \begin{cases} 1, & -\pi(2 + b) \leq x \leq \pi(2 - b) \\ 0, & \text{otherwise} \end{cases}$$

and H is a skew function, which adjusts the relative weights of the three peaks of the matched filter:

$$H(x, a, b, c) = (V(x, a, b, c) \odot (x + b\pi))^2 + a$$

$$V(x, a, b, c) = \begin{cases} xm \dfrac{\cos c}{\cos \frac{\pi}{4}}, & x < -b\pi \\ xm \dfrac{\cos\left(\frac{\pi}{2} - c\right)}{\cos \frac{\pi}{4}}, & x \geq -b\pi \end{cases}$$

$$m = \frac{\text{abs}\left(c - \frac{\pi}{4}\right)}{25\pi} \sqrt{a}$$

Figure 18:
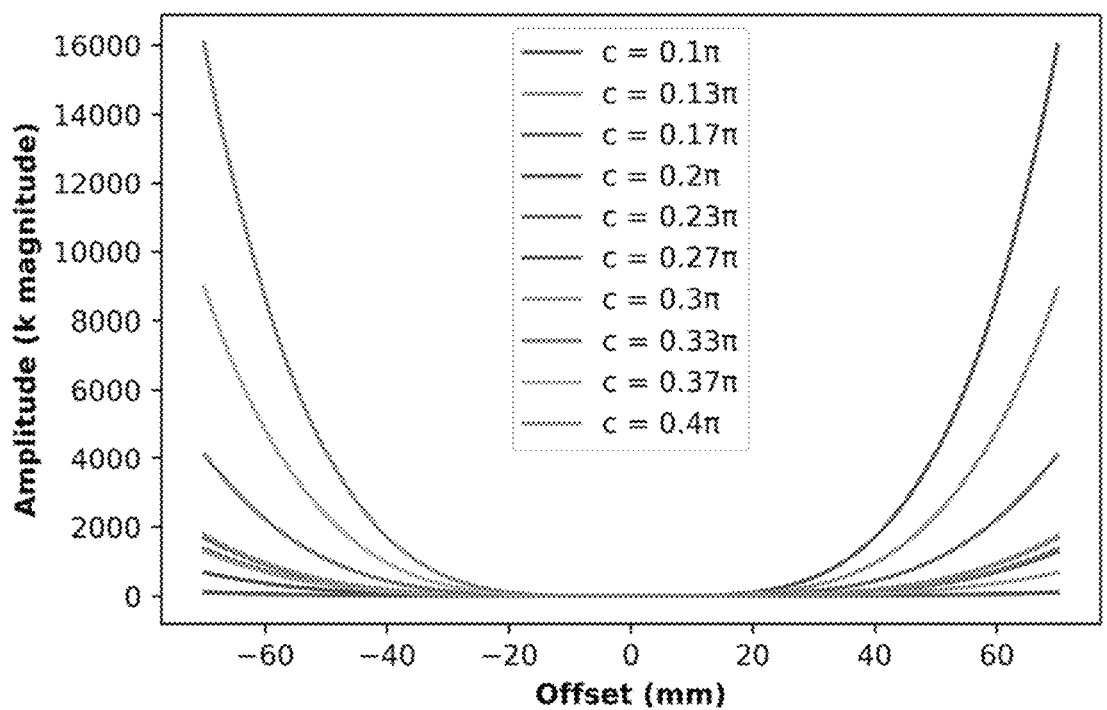
FIG. 18 shows examples of the skew function.
Figure 19:
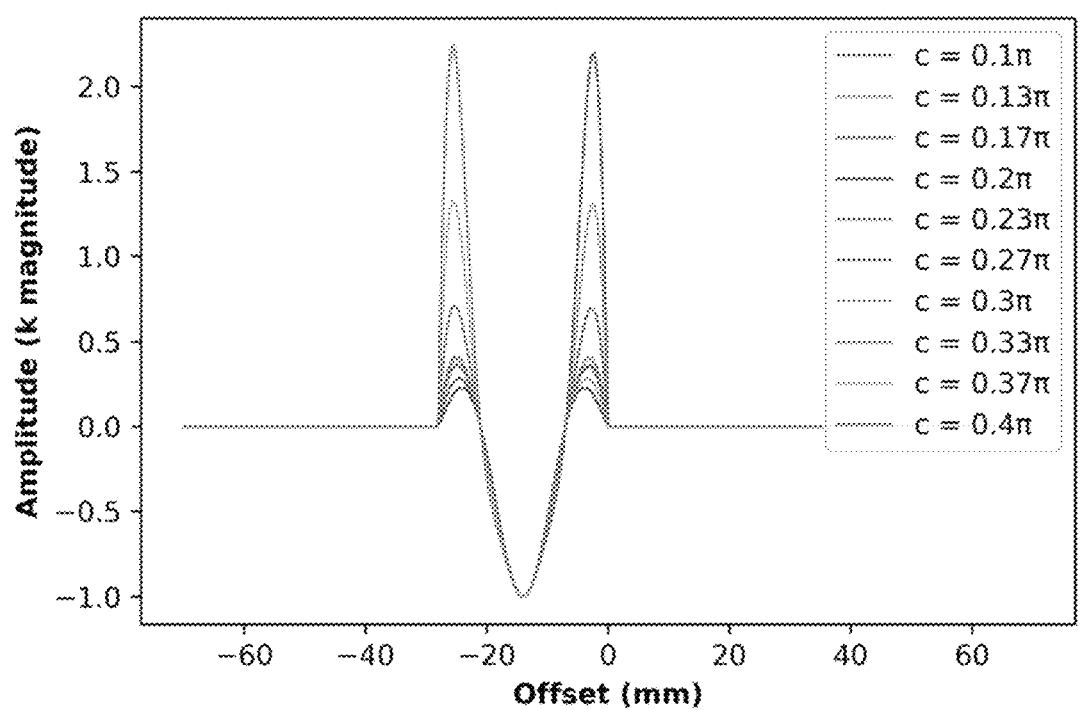
FIG. 19 shows examples of the matched filter, for solving the model of FIG. 10.

FIG. 18 shows examples of the skew function H(x, a, b, c) for $a=1$, $b=0$ and $0.1\pi \leq c \leq 0.4\pi$. FIG. 19 shows examples of the matched filter F(x, a, b, c) for $a=1$, $b=2$ and $0.1\pi \leq c \leq 0.4\pi$. Note that the value of b denotes the position of the negative peak of the function, which indicates the lead offset in electrode spacings (E). The x-axis in FIG. 19 is transformed into millimetres (7E).

The matched filter is fit to each proposed solution such that the error vector (err) is minimised by finding optimal values for the parameters a, b, c:

$$err = (F(x, a, b, c) - K)^2$$

where K is one of the proposed solution vectors $k_{1*4i}$, $k_{2*4i}$, $k_{2i*4i}$, or $k_{1i*2i}$.

The resulting optimised values of the parameters a, b, c are highly dependent on the fitting algorithm used to perform the minimisation, the initial values for each parameter that the algorithm is given and the bounds specified for each parameter. Accordingly, for the implementation of the matched filter described here, the initial values the parameters may be set as:

$$a_0 = \sqrt{\frac{|\max K - \min K|}{2}}$$

$$b_0 = \mathrm{argmin} K(x)$$

$$c_0 = \frac{\pi}{4}$$

The bounds (min, max) for each parameter may be set as:

$$a: \frac{a_0}{10}, 2a_0$$

$$b: -10, 10$$

$$c: \frac{\pi}{10}, \frac{2\pi}{5}$$

The parameter optimisation may be performed using a Trust Region Reflective algorithm, as implemented by the scipy python distribution, which is a form of step-restricted hill climbing algorithm.

One of the values of the parameter h may be selected from the four matched filters fit to the four proposed solution vectors to provide the final estimate of lead offset. In one implementation, the selected value of b may be taken from the matched filter that resulted in the lowest magnitude error during the parameter fitting.

Figure 20:
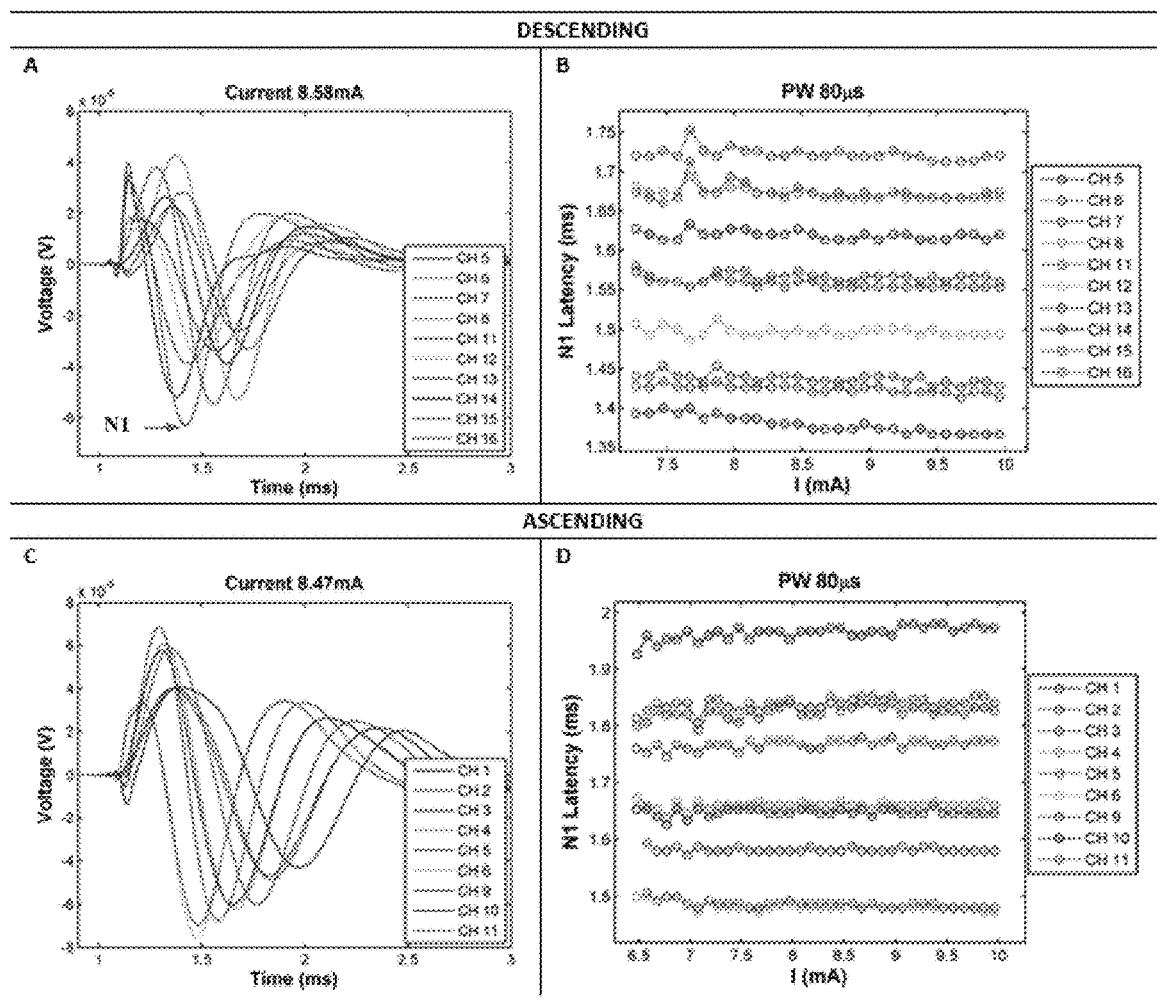
FIG. 20 shows descending (antidromic) and ascending (orthodromic) latency data.
Figure 21:
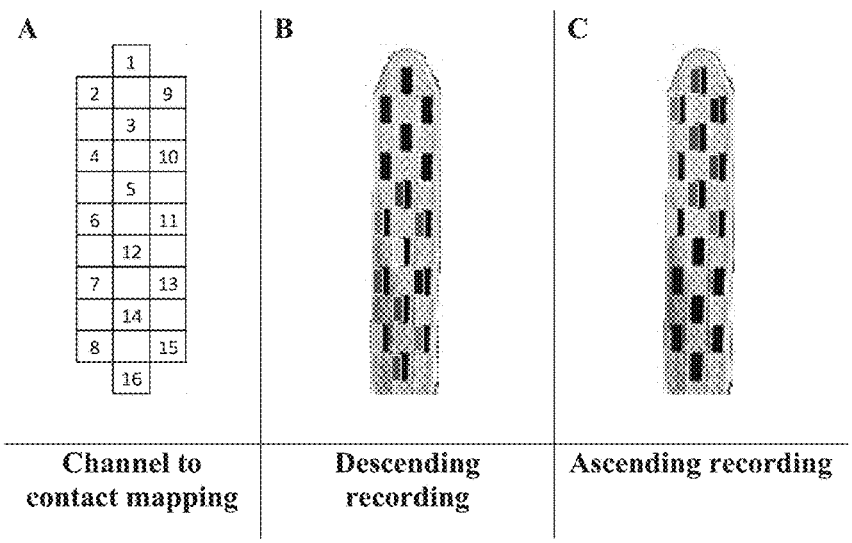
FIG. 21 shows the electrode array used for the recordings of FIG. 20.

A further aspect of the invention provides for lead offset determination using ECAP latency, that is, the time of arrival of a certain feature of the ECAP at a sense electrode. ECAP latency does not significantly change when recording laterally on contacts (electrodes) that are horizontally aligned and in the same orientation with respect to the midline of the spinal cord (or other nerve being addressed). The electrodes with a similar ECAP latency (typically referring to the N1 peak, see FIG. 20) are thus (the most) aligned with respect to the midline of the spinal cord (FIG. 20). Therefore, to estimate the offset between contacts on a lead (FIG. 21), or offset between multiple leads (FIG. 22), a device may stimulate at a fixed location and record the ECAP signal on one or more other available (unused) electrodes. Furthermore, as the separation between successive contacts on a lead is known, the difference in ECAP latency can be used to estimate the vertical distance between contacts on two leads.

To give an example, say Lead 1 and Lead 2 have 12 contacts, 3 mm in length with 4 mm spacing (i.e. pitch of 7 mm). The respective ECAP N1 peak latencies at E6, E7 (sixth and seventh contacts on Lead 1), and E4 ($4^{th}$ contact on Lead 2) respectively, namely t_E6, t_E7, and t_E4, may be measured. The ECAP latency on E4 falls between the ECAP latency of E6 and E7. It is known that Distance (d)=Speed (s)*Time (t). The distance d_lead1 between E6 and E7 is known to be 7 mm. The conduction velocity of the ECAP may be estimated as s_lead1=7/(t_E7−t_E6), and then the distance d between E6 (Lead 1) and E4 (Lead 2) may be estimated as d=s_lead1*(t_E4−t_E6).

In another example, FIGS. 20A and B show descending (antidromic) data, stimulating on CH1 and CH2 with CH1 as the cathode. FIG. 20A shows the resulting ECAP signal propagating along several recording channels (electrodes 5 through 16). FIG. 20B shows the N1 peak latency calculated at several current levels over multiple recording channels.

FIGS. 20C and D show ascending (orthodromic) data, stimulating on CH15 and CH16 with CH16 as the cathode. FIG. 20C shows the ECAP signal propagating along several recording channels (electrodes 1 through 11). FIG. 20C shows the N1 peak latency calculated at several current levels over multiple recording channels.

FIG. 21A shows the electrode array used for the recording in FIG. 20, with contacts numbered as indicated (electrodes facing the cord). FIG. 21B shows the contacts coloured to match the recordings in FIGS. 20A and 20B. FIG. 21C shows the contacts coloured to match the recordings in FIGS. 20C and 20D.

Figure 22:
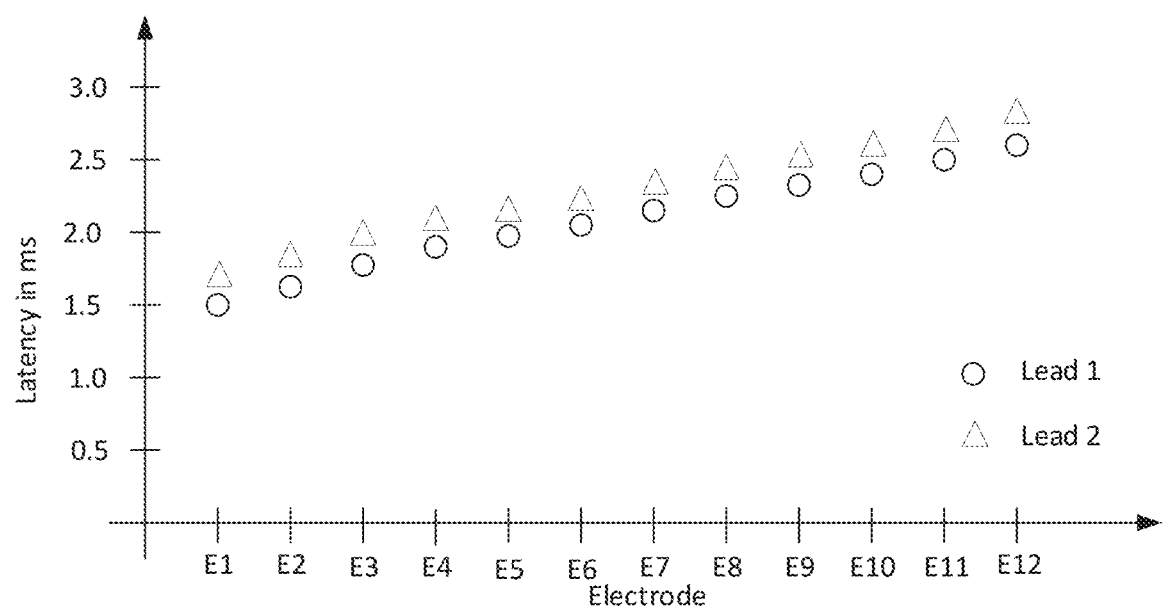
FIG. 22 is a plot of ECAP latency, and the latency offset between two leads.

This same concept can be applied to estimating the offset between two leads. In FIG. 22 the ECAP latency is offset by a constant amount across the contacts of Lead 1 and Lead 2 (suggesting they stay within the same orientation with respect to the midline of the spinal cord, i.e. are parallel to each other), being greater on Lead 2. In cases where the ECAP latency is observed to have an offset which changes along the leads, this may permit determination of a mediolateral divergence or convergence of the leads with respect to each other, being a deviation from a parallel alignment of the leads, indicating lateral migration. The spacing between each contact on the leads is known, and E1 on Lead 2 has a latency between E2 and E3 on Lead 1. Thus, E1 on Lead 2 sits within the span of those two contacts. The same technique described previously can also be applied here to obtain an estimate of the lead offset. This technique can also be applied to multiple electrode locations in order to obtain a more robust estimate using multiple ECAP latency measurements.

When seeking to measure ECAPs, for example to effect closed-loop feedback-controlled operation, it is desirable for the applied stimulus and for the recording electrode configuration to be selectively configured such that stimulus artefact is minimised in the measurements, in order to ease the task of ECAP detection. This is as taught for example in the above-noted WO2020/082126 and in WO2017/219096. In contrast, it is to be specifically noted that some embodiments of the present invention instead seek to configure the stimulation and/or recordings in a manner which enhances or maximises the generation of stimulus artefact, in order to improve a signal to noise ratio of lead offset determinations based on measurements of the stimulus artefact itself.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. An implantable device for lead offset determination, the device comprising:
    a first electrode lead comprising a first plurality of electrodes;
    a second electrode lead comprising a second plurality of electrodes;
    a stimulus source for providing a stimulus to be delivered from one or more stimulus electrodes to tissue proximal to one or more stimulus electrodes, the one or more stimulus electrodes being selected from the first plurality of electrodes and the second plurality of electrodes;
    measurement circuitry for recording from one or more sense electrodes a signal sensed from the tissue and resulting from the stimulus, the one or more sense electrodes being selected from the first plurality of electrodes and the second plurality of electrodes;

wherein at least one electrode of the first plurality of electrodes serves as either a stimulus electrode or as a sense electrode, and wherein at least one electrode of the second plurality of electrodes serves as either a stimulus electrode or as a sense electrode; and a processor configured to process the signal from the measurement circuitry in order to produce a measure of a stimulus artefact present in the signal; and the processor further configured to process the measure of the stimulus artefact to produce a measure of an offset between the first electrode lead and the second electrode lead.

2. The implantable device of claim 1, wherein a stimulus phase configuration is selected to maximise a stimulus artefact resulting from application of the stimulus.

3. The implantable device of claim 2, wherein the stimulus phase configuration comprises a biphasic pulse.

4. The implantable device of claim 2 wherein the stimulus phase configuration comprises a triphasic stimulus in which a ratio of charge of a first phase relative to a third phase is selected to effect increased stimulus artefact.

5. The implantable device of claim 1, wherein a stimulus electrode configuration is selected to spatially constrain a maximal region of a stimulus artefact resulting from application of the stimulus.

6. The implantable device of claim 5 wherein a shielded anode tripolar stimulus electrode configuration is selected.

7. The implantable device of claim 1 wherein the device is configured to provide stimuli repeatedly to be delivered from unchanged stimulus electrodes and with iteratively altered selection of sense electrode.

8. The implantable device claim 1 wherein the processor is configured to produce the measure of the offset by applying a distance-squared analytical model to measures of stimulus artefact obtained from at least two sense electrodes.

9. The implantable device of claim 8 wherein the model comprises a relationship:

$$A(d) = \frac{a}{(d-b)^2 + c^2}$$

where A (d) is a function of measured stimulus artefact A relative to a distance d of the sense electrode from the stimulus electrode, and a, b and c are fitting parameters, with b constituting the measure of the offset.

10. The implantable device of claim 9, further configured to apply an iterative fitting process to seek values for a, b and c which best fit the model to the measures of stimulus artefact.

11. The implantable device of claim 1 wherein the processor is configured to produce the measure of the offset by applying a fractional pole components model of artefact, in which each edge of each voltage step in the tissue resulting from the delivered stimulus is treated as a singularity at which is defined an independent set of step and impulse components based on a constant phase element (CPE) characterisation of an interface between the tissue and the one or more sense electrodes.

12. The implantable device of claim 1, wherein the measure of the offset comprises a measure of a rostro-caudal offset between the first electrode lead and the second electrode lead.

13. A method for lead offset determination, the method comprising:

delivering a stimulus from one or more stimulus electrodes to tissue proximal to the one or more stimulus electrodes, the one or more stimulus electrodes being selected from a first plurality of electrodes of a first electrode lead and a second plurality of electrodes of a second electrode lead;

recording from one or more sense electrodes a signal sensed from the tissue and resulting from the stimulus, the one or more sense electrodes being selected from the first plurality of electrodes and the second plurality of electrodes;

wherein at least one electrode of the first plurality of electrodes serves as either a stimulus electrode or as a sense electrode, and wherein at least one electrode of the second plurality of electrodes serves as either a stimulus electrode or as a sense electrode; and processing the signal in order to produce a measure of a stimulus artefact present in the signal; and processing the measure of the stimulus artefact to produce a measure of an offset between the first electrode lead and the second electrode lead.

14. The method of claim 13, wherein a stimulus phase configuration is selected to maximise a stimulus artefact resulting from application of the stimulus.

15. The method of claim 14, wherein the stimulus phase configuration comprises a biphasic pulse.

16. The method of claim 14 wherein the stimulus phase configuration comprises a triphasic stimulus in which a ratio of charge of a first phase relative to a third phase is selected to effect increased stimulus artefact.

17. The method of claim 13, wherein a stimulus electrode configuration is selected to spatially constrain a maximal region of a stimulus artefact resulting from application of the stimulus.

18. The method of claim 17 wherein a shielded anode tripolar stimulus electrode configuration is selected.

19. The method of claim 13 further comprising delivering stimuli repeatedly from unchanged stimulus electrodes and with iteratively altered selection of sense electrode.

20. The method of claim 13 further comprising producing the measure of the offset by applying a distance-squared analytical model to measures of stimulus artefact obtained from at least two sense electrodes.

21. The method of claim 20 wherein the model comprises a relationship:

$$A(d) = \frac{a}{(d-b)^2 + c^2}$$

where A(d) is a function of measured stimulus artefact A relative to a distance d of the sense electrode from the stimulus electrode, and a, b and c are fitting parameters, with b constituting the measure of the offset.

22. The method of claim 21, further comprising applying an iterative fitting process to seek values for a, b and c which best fit the model to the measures of stimulus artefact.

23. The method of claim 13 further comprising producing the measure of the offset by applying a fractional pole components model of artefact, in which each edge of each voltage step in the tissue resulting from the delivered stimulus is treated as a singularity at which is defined an independent set of step and impulse components based on a constant phase element (CPE) characterisation of an interface between the tissue and the one or more sense electrodes.

24. The method of claim 13, wherein the measure of the offset comprises a measure of a rostro-caudal offset between the first electrode lead and the second electrode lead.

25. A non-transitory computer readable medium for lead offset determination, comprising instructions which, when executed by one or more processors, causes performance of the following:

delivering a stimulus from one or more stimulus electrodes to tissue proximal to the one or more stimulus electrodes, the one or more stimulus electrodes being selected from a first plurality of electrodes of a first electrode lead and a second plurality of electrodes of a second electrode lead;

recording from one or more sense electrodes a signal sensed from the tissue and resulting from the stimulus, the one or more sense electrodes being selected from the first plurality of electrodes and the second plurality of electrodes;

wherein at least one electrode of the first plurality of electrodes serves as either a stimulus electrode or as a sense electrode, and wherein at least one electrode of the second plurality of electrodes serves as either a stimulus electrode or as a sense electrode; and processing the signal in order to produce a measure of a stimulus artefact present in the signal; and processing the measure of the stimulus artefact to produce a measure of an offset between the first electrode lead and the second electrode lead.

26. The non-transitory computer readable medium claim 25, wherein the instructions contained upon the non-transitory computer readable medium comprise a clinical programming application, the clinical programming application further configured to provide clinical programming functions for an implantable device comprising the first and second electrode leads, so as to program the implantable device based on the measure of the offset.

* * * * *